US010278912B2

(12) United States Patent
Coragliotti et al.

(10) Patent No.: US 10,278,912 B2
(45) Date of Patent: *May 7, 2019

(54) MICROALGAL POLYSACCHARIDE COMPOSITIONS

(71) Applicant: Algenist Holdings, Inc., Westport, CT (US)

(72) Inventors: Anna Coragliotti, San Francisco, CA (US); Scott Franklin, Woodside, CA (US); Anthony G. Day, San Francisco, CA (US); Stephen M. Decker, San Francisco, CA (US)

(73) Assignee: Algenist Holdings, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,138

(22) Filed: Nov. 25, 2014

(65) Prior Publication Data

US 2015/0150776 A1    Jun. 4, 2015

Related U.S. Application Data

(63) Continuation of application No. 13/260,546, filed as application No. PCT/US2010/029081 on Mar. 29, 2010, now Pat. No. 8,927,522, which is a continuation-in-part of application No. PCT/US2009/060692, filed on Oct. 14, 2009.

(60) Provisional application No. 61/164,312, filed on Mar. 27, 2009, provisional application No. 61/105,121, filed on Oct. 14, 2008, provisional application No. 61/157,187, filed on Mar. 3, 2009, provisional application No. 61/173,166, filed on Apr. 27, 2009, provisional application No. 61/246,070, filed on Sep. 25, 2009.

(51) Int. Cl.
| | | |
|---|---|---|
| A61K 31/715 | (2006.01) |
| C08B 37/00 | (2006.01) |
| C12P 19/04 | (2006.01) |
| A61K 8/73 | (2006.01) |
| A61Q 19/08 | (2006.01) |
| A61K 8/02 | (2006.01) |
| C08L 5/00 | (2006.01) |
| A61K 8/9706 | (2017.01) |

(52) U.S. Cl.
CPC .............. *A61K 8/73* (2013.01); *A61K 8/0241* (2013.01); *A61K 8/9706* (2017.08); *A61Q 19/08* (2013.01); *C08B 37/0003* (2013.01); *C08B 37/006* (2013.01); *C08B 37/0036* (2013.01); *C08L 5/00* (2013.01); *C12P 19/04* (2013.01); *A61K 2800/412* (2013.01); *A61K 2800/654* (2013.01); *Y10T 428/2982* (2015.01)

(58) Field of Classification Search
CPC .. A61K 8/73; A61K 8/0241; A61K 2800/412; C08B 37/006; C12P 19/04

USPC ................. 514/54; 536/123.1, 123; 435/101
See application file for complete search history.

(56) References Cited

U.S. PATENT DOCUMENTS

| | | |
|---|---|---|
| 3,981,996 A | 9/1976 | Leigh |
| 3,983,008 A | 9/1976 | Shinozaki et al. |
| 4,373,434 A | 2/1983 | Alexander et al. |
| 4,417,415 A | 11/1983 | Cysewski et al. |
| 4,742,164 A | 5/1988 | Iguchi et al. |
| 4,901,635 A | 2/1990 | Williams |
| 4,906,746 A | 3/1990 | Barnier et al. |
| 5,089,481 A | 2/1992 | Muto et al. |
| 5,198,217 A | 3/1993 | Vedros |
| 5,338,673 A | 8/1994 | Thepenier et al. |
| 5,401,504 A | 3/1995 | Das et al. |
| 5,508,033 A | 4/1996 | Briand |
| 5,521,090 A | 5/1996 | Doncheck et al. |
| 5,643,585 A | 7/1997 | Arad et al. |
| 5,658,767 A | 8/1997 | Kyle |
| 5,680,812 A | 10/1997 | Linsgeseder |
| 5,685,218 A | 11/1997 | Kemper |
| 5,826,500 A | 10/1998 | Kemper |
| 5,878,747 A | 3/1999 | Enomoto et al. |
| 5,916,577 A | 6/1999 | Golz et al. |
| 6,166,231 A | 12/2000 | Hoeksema |
| 6,328,987 B1 | 12/2001 | Marini |
| 6,440,431 B1 | 8/2002 | Yoshida et al. |
| 6,551,596 B2 | 4/2003 | Kralovec |
| 6,680,062 B2 | 1/2004 | Muizzuddin et al. |
| 6,750,048 B2 | 6/2004 | Ruecker et al. |

(Continued)

FOREIGN PATENT DOCUMENTS

| | | |
|---|---|---|
| EP | 0996740 B1 | 9/2005 |
| JP | 04-222593 A | 8/1992 |

(Continued)

OTHER PUBLICATIONS

Baba et al.; JP 2004002582 A; Jan. 1, 2004 (Machine English Translation).*

(Continued)

*Primary Examiner* — Shaojia A Jiang
*Assistant Examiner* — Michael C. Henry
(74) *Attorney, Agent, or Firm* — Locke Lord LLP

(57) ABSTRACT

Provided herein are microalgal polysaccharide compositions and. Also provided are methods of using polysaccharides for applications such as topical personal care products, cosmetics, and wrinkle reduction compositions. The invention also provides novel microalgal compositions useful for improving the health and appearance of skin. The invention also includes insoluble polysaccharide particles for application to human skin.

18 Claims, 4 Drawing Sheets
Specification includes a Sequence Listing.

(56) References Cited

U.S. PATENT DOCUMENTS

| | | | |
|---|---|---|---|
| 6,767,899 | B1 | 7/2004 | Kay et al. |
| 7,025,966 | B2 | 4/2006 | Majmudar |
| 7,037,697 | B2 | 5/2006 | Kumar et al. |
| 7,063,957 | B2 | 6/2006 | Chen |
| 7,135,290 | B2 | 11/2006 | Dillon |
| 7,351,558 | B2 | 4/2008 | Ruecker et al. |
| 7,662,598 | B2 | 2/2010 | Ruecker et al. |
| 7,678,931 | B2 | 3/2010 | Fichtali et al. |
| 7,781,193 | B2 | 8/2010 | Ruecker et al. |
| 8,277,849 | B2 | 10/2012 | Dillon et al. |
| 8,298,548 | B2 | 10/2012 | Avila et al. |
| 8,557,249 | B2 | 10/2013 | Brooks et al. |
| 8,927,522 | B2 | 1/2015 | Coragliotti et al. |
| 8,932,652 | B2 | 1/2015 | Dillon et al. |
| 2001/0055627 | A1 | 12/2001 | Guthrie et al. |
| 2003/0078233 | A1 | 4/2003 | Arad et al. |
| 2003/0134803 | A1 | 7/2003 | Cherr et al. |
| 2003/0198730 | A1 | 10/2003 | Stewart |
| 2003/0207947 | A1 | 11/2003 | Desouza et al. |
| 2004/0168648 | A1 | 9/2004 | Ayers |
| 2004/0180126 | A1 | 9/2004 | Kies |
| 2004/0185063 | A1 | 9/2004 | Ray |
| 2004/0197790 | A1 | 10/2004 | Stanton et al. |
| 2004/0228875 | A1 | 11/2004 | Leclerc et al. |
| 2005/0042355 | A1 | 2/2005 | Perlman et al. |
| 2005/0089501 | A1 | 4/2005 | Berardesca et al. |
| 2005/0106657 | A1 | 5/2005 | Rodriguez et al. |
| 2005/0123499 | A1 | 6/2005 | Majmudar |
| 2005/0129831 | A1 | 6/2005 | Fabritius |
| 2005/0171053 | A1 | 8/2005 | Blakemore et al. |
| 2005/0239742 | A1 | 10/2005 | Place et al. |
| 2005/0261240 | A1 | 11/2005 | Maguire et al. |
| 2006/0122410 | A1 | 6/2006 | Fichtali et al. |
| 2006/0183184 | A1 | 8/2006 | Bosley et al. |
| 2006/0210523 | A1 | 9/2006 | Majmudar |
| 2006/0233845 | A1 | 10/2006 | Lukowski et al. |
| 2006/0286205 | A1 | 12/2006 | Fichtali et al. |
| 2007/0166266 | A1 | 7/2007 | Dillon et al. |
| 2007/0166449 | A1 | 7/2007 | Dillon et al. |
| 2007/0166797 | A1 | 7/2007 | Dillon et al. |
| 2007/0167396 | A1 | 7/2007 | Dillon et al. |
| 2007/0167397 | A1 | 7/2007 | Dillon et al. |
| 2007/0167398 | A1 | 7/2007 | Dillon et al. |
| 2007/0191303 | A1 | 8/2007 | Dillon et al. |
| 2007/0297996 | A1 | 12/2007 | Tanner |
| 2008/0124286 | A1 | 5/2008 | Lisson |
| 2008/0206274 | A1 | 8/2008 | Majmudar et al. |
| 2009/0004715 | A1 | 1/2009 | Trimbur et al. |
| 2009/0017058 | A1 | 1/2009 | Arad et al. |
| 2009/0069213 | A1* | 3/2009 | Avila .............. A61K 8/975 514/1.1 |
| 2009/0274736 | A1 | 11/2009 | Dillon et al. |
| 2009/0285850 | A1 | 11/2009 | Dillon et al. |
| 2009/0305942 | A1 | 12/2009 | Day et al. |
| 2011/0124544 | A1 | 5/2011 | He et al. |
| 2012/0264177 | A1 | 10/2012 | Avila et al. |
| 2014/0170184 | A1 | 6/2014 | Brooks et al. |

FOREIGN PATENT DOCUMENTS

| | | | |
|---|---|---|---|
| JP | 2002069443 | A | 8/2002 |
| JP | 2004002582 | A * | 1/2004 |
| WO | WO 97/000689 | A1 | 1/1997 |
| WO | WO 00/075282 | A1 | 12/2000 |
| WO | WO 01/81603 | A2 | 11/2001 |
| WO | WO 02/011746 | A2 | 2/2002 |
| WO | WO 03/041679 | A2 | 5/2003 |
| WO | WO 03/072775 | A1 | 9/2003 |
| WO | WO 04/108941 | A1 | 12/2004 |
| WO | WO 07/066340 | A1 | 6/2007 |
| WO | WO 07/084769 | A2 | 7/2007 |
| WO | WO 07/136428 | A2 | 11/2007 |
| WO | WO 10/054322 | A1 | 5/2010 |
| WO | WO 10/111710 | A1 | 9/2010 |

OTHER PUBLICATIONS

"Buffer solution," Wikipedia, the free encyclopedia, 1-6, (2011). [Retrieved from the Internet May 11, 2011: <http ://en.wikipedia.org/wiki/Buffer_solution>].

"Guidance for Industry: Container Closure Systems for Packaging Human Drugs and Biologics", U.S. Department of Health and Human Services, Food and Drug Administration, 1-35, (1999).

"All Natural Food Mask," The Raw Food Institute, 2 pages, (2013). [Retrieved from the Internet May 20, 2013: <URL: http://http://therawfoodinistitute.com/raw-food-articles/all-natural-food-mask/>].

Alignments, Sequence Search report, GenBank ACQ5U8S3_9RHOD dated Dec. 7, 2004.

Allen et al., "Carotenoid Distribution in Certain Naturally Occurring Algae and in some Artificially Induced Mutants of Chlorella pyrenoidosa," *J. gen. Microbial.*, (23)98-108, (1960).

Ansel et al., *Pharmaceutical Dosage Forms and Drug Delivery Systems*, published by Lippincott Williams & Wilkins, p. 55-56 (1999).

Arad et al., "Effects of Nitrogen on Polysaccharide Production in a Porphyridium," *Applied and Environmental Microbiology*, 54(10):2411-2414 (1988).

Baumann, "How to Prevent Photoaging?," *Journal of Investigative Dermatology*,125:xii-xiii, (2005).

Becker, "Microalgae in Human and Animal Nutrition," *Handbook of Microalgal Culture*, Blackwell, p. 312-351, (2004).

Césarini et al., "Immediate Effects of UV Radiation on the Skin: Modification by an Antioxidant Complex Containing Carotenoids", *Photoderm., Photoimmun. & Photomed.* 19:182-189 (2003).

Conti et al., "Seasonal influences on stratum corneum ceramide 1 fatty acids and the influence of topical essential fatty acids," *International Journal of Cosmetics Science*, 18:1-12, (1996).

Dallimore, "Perfumery," *Chemistry and Technology of the Cosmetics and Toiletries Industry*, edited by D.F. Williams and W.H. Schmitt, published by Chapman & Hall, 258-259, (1992).

Dvir et al., "Soluble polysaccharide and biomass of red microalgal *Porphyridium* sp. alter intestinal morphology and reduce serum cholesterol in rats", *British J Nutrition* 84(4):469-476, (2000).

El-Sheekh et al., "Variation of Some Nutritional Constituents and Fatty Acid Profiles of Chlorella vulgaris Beijerinck Grown under Auto and Heterotrophic Conditions," International Journal of Botany, 5(2):153-159, (2009).

EPO Application No. EP 10756997.2, Supplementary European Search Report and European Search Opinion, dated Jul. 23, 2014.

EPO Supplementary European Search Report and European Search Opinion for application EP07718342 dated Nov. 7, 2012.

Eteshola et al., "Red microalga exopolysaccharides: 2. Study of rheology, morphology and thermal gelation of aqueous preparations," *Acta Polym.*, 49:549-556, (1998).

Fabregas et al., "In vitro inhibition of the replication of haemorrhagic septicaemia virus (VHSV) and African swine fever virus (ASFV) by extracts from marine microalgae," Antiviral Research, 44:67-73, (1999).

Ficner et al, "Isolation, Crystallization, Crystal Structure Analysis and refinement of B-Phycoerythin from the Red Alga Pophyridium sordidum at 2.2 A Resolution", *J. Mol. Biol.* 228(3):935-950, (1992).

Gennaro, *Remington: The Science and Practice of Pharmacy* Lippincott Williams & Wilkins, 20th edition, p. 1017-1020 and 1694-1699. (2000).

Geresh, et al., "Characterization of the extracellular polysaccharide of *Porphyridium* sp. molecular weight determination and rheological properties", *Carbohydrate Polymers* 50:183-189, (2002).

Geresh, et al., "The extracellular polysaccharide of the Red Microalgae: Chemistry and Rheology", *Bioresource Technology* 38(2-3):195-201, (1991).

Gloaguen et al., "The extracellular polysaccharide of *Porphyridium* sp.: an NMR study of lithium-resistant oligosaccharidic fragments," *Carbohydrate Research*, 339:97-103, (2004).

Gourdon, D. et al. Lubrication by the red microalgae *Porphyridium* sp. polysaccharide: American Physical Society, March Meeting,

(56) References Cited

OTHER PUBLICATIONS

Mar. 21-25, 2004, Palais de Congres de Montreal, Montreal, Quebec, Canada, Meeting ID: MAR04, abstract #H8.009—English Abs.
Gourdon, D. et al. "Superlubricity of a natural polysaccharide from the alga *Porphyridium* sp.," *American Physical Society, APS March Meeting*, Mar. 21-25, 2005 abstract #V31.010—English Abstract only.
Greul et al., "Photoprotection of UV-Irradiated Human Skin: An Antioxidative Combination of Vitamins E and C, Carotenoids, Selenium and Proanthocyanidins," *Skin Pharmacology and Applied Skin Physiology*, 15:307-315, (2002).
Guerin et al., "Haematococcus astaxanthin: applications for human health and nutrition," *TRENDS in Biotechnology*, 21(5):210-216, (2003).
Guil-Guerrero et al., "Functional properties of the biomass of three microalgal species", *J. Food Engin.* 65:511-517, (2004).
Guzman et al., "Anti-inflammatory and Immunomodulatory Activities of Polysaccharide from Chlorella stigmatophora and Phaeodactylum tricornutum", *Phytother. Res.* 17:665-670, (2003).
Holzer, "Water, pH and buffers," *Georgia Tech Prism Web Pages*, 1-6, (2002). [Retrieved from the Internet Jan. 2011: <http ://www.prism.gatech.edu/-gh19/b1510/water.htm>].
Huheihel, M. et al. "Activity of *Porphyridium* sp. polysaccharide against herpes simplex viruses in vitro and in vivo" *J. Biochem. Biophys. Methods* Jan. 4, 2002;50(2-3):189-200.
International Preliminary Report on Patentability for PCT/US2007/001653 dated Sep. 9, 2008.
International Preliminary Report on Patentability for PCT/US2007/001319 dated Oct. 21, 2008.
International Preliminary Report on Patentability for PCT/US2010/029081 dated Sep. 27, 2011.
International Search Report and Written Opinion for PCT/US2007/001319 dated Sep. 19, 2008.
International Search Report and Written Opinion for PCT/US2007/001653 dated Jul. 28, 2008.
International Search Report or PCT/US2010/029081 dated May 27, 2010.
Kamiya, "Effects of Blue Light and Ammonia on Nitrogen Metabolism in a Colorless Mutant of Chlorella," Plant Celli Physiol., 30(4):513-521, (1989).
Kruckeberg et al., "The HXT2 gene of *Saccharomyces cerevisiae* is required for high-affinity glucose transport", *Mol. Cell. Biol.* 10(11):5903-5913, (1990).
Lapidot, M. et al. "Stable Chloroplast Transformation of the Unicellular Red Alga *Porphyridium* Species", Plant Physiol. May 2002;129(1):7-12.
Lee et al., "Dietary Lutein Reduces Ultraviolet Radiation-Induced Inflammation and Immunosuppression", *J. Invest. Dermatol.* 122:510-517, (2004).
Leffingwell et al., "Cooling Ingredients and Their Mechanism of Action," *Handbook of Cosmetic Science and Technology*, 3rd ed., Informa Healthcare, pp. 661-675, (2009).
Liang et al., "Current microalgal health food R&D activities in China", *Hydrobiologia* 512:45-48, (2004).
Matsui et al., "Sulfated polysaccharides from Red Microalgae Have Antiinflammatory Properties In Vitro and In Vivo," *Applied Biochemistry and Biotechnology*, 104:13-22, (2003).
Merchuk et al. "Light/Dark Cycles in the Growth of the Red Microalga *Porphyridium* Sp.". Biotechnol Bioeng. Sep. 20, 1998;59(6):705-13.
Mitsuhashi et al, "X-Ray Structure of Beta-Carbonic Anhydrase from the Red Alga, *Porphyridium purpureum*, Reveals a Novel Catalytic Site for CO2 Hydration", *J. Biol. Chem.* 275(8):5521-5526, (2000).
Miyachi, *World Catalogue of Algae*, 2nd Edition. Edited by Shigetoh, Miyachi, published by the Japan Scientific Societies Press, p. 58-74 (1989).
Muggli, "Systemic evening primrose oil improves the biophysical skin parameters of healthy adults", *Intl. J. Cosmetic Sci.* 27:243-249, (2005).

NCB' submission L43357, "Chlorella vulgaris chloroplast large subunit ribosomal RNA (rrnL) gene," [online], (2005). [Retrieved from the Internet May 14, 2010: <URL: http://www.ncbi.nlm.nih.gov/nuccore/17028301>].
Nghiem, et al., "Ultraviolet A Radiation Suppresses an Established Immune Response: Implications for Sunscreen Design", *J. Invest. Derm.* 117(5):1193-1198 (2001).
Olaitan et al., "Polysaccharides of Chlorella pyrenoidosa," *Biochem. J.* 82:509-519, (1962).
PCT International Preliminary Report on Patentability (Chapter I) dated May 10, 2011 for application PCT/US09/63740.
PCT Search Report dated Mar. 2, 2010 for application PCT/US09/63740.
Petit et al., "Ultrasonic depolymerization of an exopolysaccharide produced by a bacterium isolated from a deep-sea hydrothermal vent polychaete annelid," Ultrasonics Sonochemistry, 14(2):107-112, (2007).
Primavera et al., "Clinical and instrumental evaluation of a food supplement in improving sking hydration", *Intl. J. Cosmetic Science* 27:199-204, (2005).
Pulz et al., "Valuable products from biotechnology of microalgae," *Appl Microbiol Biotechnol*, 65:635-648, (2004).
Rudnic et al., "Oral Solid Dosage Forms" in *Remington's Pharmaceutical Sciences*, 18th Edition, editor Alfonso R. Gennaro, published by Mack Publishing Company, p. 1633-1638 (1990).
Sansawa et al., "Production of Intracellular Phytochemicals in Chlorella under Heterotrophic Conditions," *J Biosci. Bioeng.*, 98(6):437-444, (2004).
Scipio, "A Red Marine Algae Sex Gel" website: http://www.antiviralgel.com/, download date Aug. 8, 2008.
Seffernick et al., "Melamine deaminase and atrazine chlorohydrolase: 98 percent identical but functionally different", *J. Bacteriology* 183(8):2405-2410, (2001).
Shrestha et al., "A glycoprotein noncovalently associated with cell-wall polysaccharide of the red microalga *Porphyridium* sp.(Rhodophyta)", *J. Phycol.* 40:568-580, (2004).
Sibbald et al., "Preparing the Wound Bed 2003: Focus on Infectin and Inflammation," *Ostomy/Wound Management.*, 49(11):24-51, (2003).
Simon-Bercovitch, et al., "Cell wall formation during the cell cycle of *Porphyridium* sp. (*Phodophyta*)", J. Phycol. 35:78-83, (1999).
Storey et al., "Eicosapentaenoic Acid and Docosahexaenoic Acid Reduce UVB- and TNF-α-induced IL-8 Secretion in Keratinocytes and UVB-induced IL-8 in Fibroblasts", *J. Invest. Dermatol.* 124:248-255, (2005).
Talyshinsky et al., "Anti-viral activity of red microalgal polysaccharides against retroviruses", *Cancer Cell Int'l.* 2(8):1-7 (2002).
Tannin-Spitz et al., "Antioxidant activity of the polysaccharide of the red microalga *Porphyridium* sp," *Journal of Applied Mycology*, 17(3):215-22, (2005).
U.S. Appl. No. 11/336,426, Examiner Interview Summary Record and Restriction Requirement dated Nov. 3, 2008.
U.S. Appl. No. 11/336,426, Examiner Interview Summary Record and Advisory Action dated Sep. 9, 2009.
U.S. Appl. No. 11/336,426, Examiner Interview Summary Record and Advisory Action dated Oct. 14, 2009.
U.S. Appl. No. 11/336,426, Examiner Interview Summary Record dated Jun. 29, 2010.
U.S. Appl. No. 11/336,426, Examiner Interview Summary Record and Abandonment Notice dated Apr. 12, 2011.
U.S. Appl. No. 11/336,426, Final Office Action dated Jun. 22, 2009.
U.S. Appl. No. 11/336,426, Non-Final Office Action dated Feb. 26, 2010.
U.S. Appl. No. 11/336,426, Non-Final Office Action dated Aug. 3, 2010.
U.S. Appl. No. 11/336,426, Restriction Requirement dated Apr. 4, 2008.
U.S. Appl. No. 11/336,428, Examiner Interview Summary Record and Abandonment Notice dated Mar. 23, 2009.
U.S. Appl. No. 11/336,428, Non-Final Office Action dated Jul. 9, 2008.
U.S. Appl. No. 11/336,428, Restriction Requirement dated Apr. 14, 2008.

(56) References Cited

OTHER PUBLICATIONS

U.S. Appl. No. 11/336,430, Examiner Interview Summary Record and Abandonment Notice dated Aug. 4, 2009.
U.S. Appl. No. 11/336,430, Restriction Requirement dated Apr. 25, 2008.
U.S. Appl. No. 11/336,430, Restriction Requirement dated Sep. 26, 2008.
U.S. Appl. No. 11/336,431, Non-Final Office Action dated Nov. 2, 2007.
U.S. Appl. No. 11/336,431, Restriction Requirement dated Mar. 30, 2007.
U.S. Appl. No. 11/336,431, Restriction Requirement dated Dec. 18, 2006.
U.S. Appl. No. 11/336,656, Non-Final Office Action dated Aug. 26, 2008.
U.S. Appl. No. 11/336,656, Restriction Requirement dated Mar. 4, 2008.
U.S. Appl. No. 11/337,103, Advisory Action dated Feb. 18, 2010.
U.S. Appl. No. 11/337,103, Advisory Action dated Apr. 6, 2010.
U.S. Appl. No. 11/337,103, Advisory Action dated Dec. 18, 2009.
U.S. Appl. No. 11/337,103, Examiner Interview Summary Record and Abandonment Notice dated Apr. 26, 2011.
U.S. Appl. No. 11/337,103, Final Office Action dated Aug. 4, 2009.
U.S. Appl. No. 11/337,103, Non-Final Office Action dated Aug. 13, 2010.
U.S. Appl. No. 11/337,103, Non-Final Office Action dated Nov. 7, 2008.
U.S. Appl. No. 11/337,103, Restriction Requirement dated Mar. 18, 2008.
U.S. Appl. No. 11/337,171, Examiner Interview Summary Record and Abandonment Notice dated Apr. 29, 2009.
U.S. Appl. No. 11/337,171, Non-Final Office Action dated Aug. 13, 2008.
U.S. Appl. No. 11/337,171, Restriction Requirement dated Mar. 5, 2008.
U.S. Appl. No. 11/932,754, Examiner Interview Summary Record dated Oct. 5, 2010.
U.S. Appl. No. 11/932,754, Final Office Action dated Aug. 9, 2011.
U.S. Appl. No. 11/932,754, Non-Final Office Action dated Dec. 23, 2010.
U.S. Appl. No. 11/932,754, Restriction Requirement dated Aug. 3, 2010.
U.S. Appl. No. 11/932,782, Advisory Action dated Sep. 16, 2010.
U.S. Appl. No. 11/932,782, Election of Species Requirement dated Aug. 16, 2011.
U.S. Appl. No. 11/932,782, Final Office Action dated May 20, 2010.
U.S. Appl. No. 11/932,782, Non-Final Office Action dated Jan. 12, 2011.
U.S. Appl. No. 11/932,782, Non-Final Office Action dated Jan. 24, 2011.
U.S. Appl. No. 11/932,782, Non-Final Office Action dated Mar. 20, 2012.
U.S. Appl. No. 11/932,782, Non-Final Office Action dated Nov. 19, 2009.
U.S. Appl. No. 11/932,782, Notice of Allowance dated Jul. 18, 2012.
U.S. Appl. No. 11/932,782, Restriction Requirement dated Jun. 26, 2009.
U.S. Appl. No. 12/176,320, Final Office Action dated Sep. 22, 2011.
U.S. Appl. No. 12/176,320, Non-Final Office Action dated Mar. 15, 2011.
U.S. Appl. No. 12/176,320, Non-Final Office Action dated Dec. 14, 2011.
U.S. Appl. No. 12/176,320, Notice of Allowance dated Sep. 4, 2012.
U.S. Appl. No. 12/176,320, Restriction Requirement dated Nov. 29, 2010.
U.S. Appl. No. 12/430,036, Final Office Action dated Aug. 2, 2011.
U.S. Appl. No. 12/430,036, Non-Final Office Action dated Dec. 14, 2010.
U.S. Appl. No. 13/128,217, Non-Final Office Action dated Mar. 29, 2013.
U.S. Appl. No. 13/128,217, Notice of Allowance dated Aug. 7, 2013.
U.S. Appl. No. 13/260,546, Final Office Action dated Jan. 30, 2014.
U.S. Appl. No. 13/260,546, Non-Final Office Action dated Jul. 1, 2013.
U.S. Appl. No. 13/260,546, Notice of Allowance dated Aug. 29, 2014.
U.S. Appl. No. 13/260,546, Requirement for Restriction/Election dated Feb. 19, 2013.
U.S. Appl. No. 13/531,419, Final Office Action dated Jan. 23, 2013.
U.S. Appl. No. 13/531,419, Non-Final Office Action dated Jun. 22, 2012.
U.S. Appl. No. 13/531,419, Non-Final Office Action dated Sep. 9, 2014.
U.S. Appl. No. 13/600,102, Non-Final Office Action dated May 13, 2014.
U.S. Appl. No. 13/600,102, Non-Final Office Action dated Dec. 10, 2013.
U.S. Appl. No. 13/600,102, Notice of Allowance dated Oct. 22, 2014.
U.S. Appl. No. 13/600,102, Restriction Requirement dated Sep. 26, 2013.
U.S. Appl. No. 14/015,921, Restriction Requirement dated May 15, 2014.
Ucko et al., "Relationship between the Unicellular Red Alga *Porphyridium* sp. and Its Predator, the *Dinoflagellate Gymnodinium* sp.," *Applied and Environmental Microbiology*, Nov. 1989, 55(11):2990-2994.
Urano, et al., "Effect of Osmotic Stabilizers on Protoplast Generation of Chlorelia ellipsoidea Yellow/White Color Mutants," Journal of Bioscience and Bioengineering, 90(5):567-569, (2000).
Van Der Meeren et al., "Abdominal Radiation Exposure Elicits Inflammatory Responses and Abscopal Effects in the Lungs of Mice", *Radiation Res.* 163:144-152, (2005).
Vinson et al., "Comparative topical absorption and antioxidant effectiveness of two forms of coenzyme Q10 after a single dose and after long-term supplementation in the skin of young and middle-aged subjects", *IFSCC Magazine* 8(4):1-6, (2005).
Wells, "Additivity of mutational effects in proteins", *Biochem.* 29(37):8509-8517, (1990).
Xu et al., "High quality biodiesel production from a microalga *Chlorella protothecoides* by heterotrophic growth in fennenters," *Journal of Biotechnology*, 126:499-507. (2006).
Yamamoto et al., "Late type of daughter cell wall synthesis in one of the Chlorellaceae, Parachlorella kessleri (Chlorophyta, Trebouxiophyceae)," *Planta*, 221:766-775, (2005).

* cited by examiner

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgttgaagaa tgagccggcg ac                                             22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtgagcta ttacgcactc                                                20

<210> SEQ ID NO 3
<211> LENGTH: 548
<212> TYPE: DNA
<213> ORGANISM: Parachlorella kessleri and Parachlorella beijerinckii

<400> SEQUENCE: 3
tgttgaagaa tgagccggcg acttagaaga agtggcttgg ttaaggataa ctatccggag    60
ccagagcgaa agcaagtctg aatagggcgc ttaaaggtca cttttctag  acccgaaccc   120 gggtgatcta accatgacca ggatgaagct tgggtaacac cacgtgaagg tccgaaccga   180
ccgatgttga aaaatcggcg gatgagttgt ggttagcggt gaaataccaa tcgaactcgg   240
agctagctgg ttctccccga aatgcgttga ggcgcagcgg tttatgaggc tgtctagggg   300
taaagcactg tttcggtgcg ggctgcgaaa gcggtaccaa atcgtggcaa actctgaata   360
ctagatatgc tattcatgag ccagtgagac ggtgggggat aagcttcatc gtcaagaggg   420
aaacagccca gatcaccagc taaggcccca aaatggtcgt taagtggcaa aggaggtgag   480
aatgctgaaa caaccaggag gtttgcttag aagcagccac cctttaaaga gtgcgtaata   540
gctcactg                                                           548

<210> SEQ ID NO 4
<211> LENGTH: 546
<212> TYPE: DNA
<213> ORGANISM: Chlorella sorokiniana

<400> SEQUENCE: 4
tgttgaagaa tgagccggcg acttagaaaa cgtggcaagg ttaaggacat gtatccggag    60
ccgaagcgaa agcaagtctg aatagggcgc ctaagtcatt ttttctagac ccgaacccgg   120
```

```
gtgatctaac catgaccagg atgaagcttg ggtgacacca agtgaaggtc cgaaccgacc      180
gatgttgaaa aatcggcgga tgagttgtgg ttagcggtga aataccagtc gaactcggag      240
ctagctggtt ctccccgaaa tgcgttgagg cgcagcggtt cataaggctg tctaggggta      300
aagcactgtt tcggtgcggg ctgcgaaagc ggtaccaaat cgtggcaaac tctgaatact      360
agatatgcta tttatgagcc agtgagacgg tgggggataa gcttcatcgt cgagagggaa      420
acagcccaga tcactagcta aggccccaaa atgatcgtta agtgacaaag gaggtgagaa      480
tgcagaaaca accaggaggt ttgcttagaa gcagccaccc tttaaagagt gcgtaatagc      540
tcactg                                                                546
```

MICROALGAL POLYSACCHARIDE COMPOSITIONS

CROSS-REFERENCE TO RELATED APPLICATIONS

This application is a continuation of U.S. application Ser. No. 13/260,546, filed Oct. 26, 2011, which is a US National Stage Application under 35 USC 371 of International Application No. PCT/US2010/029081, filed Mar. 29, 2010, now patented as U.S. Pat. No. 8,927,522, with an issue date of Jan. 6, 2016, which claims the benefit under 35 U.S.C. 119(e) of U.S. Provisional Application No. 61/164,312, filed Mar. 27, 2009, and which is also a continuation-in-part of International Application No. PCT/US2009/060692, filed Oct. 14, 2009, which claims the benefit under 35 U.S.C. 119(e) of U.S. Provisional Application No. 61/105,121, filed Oct. 14, 2008, U.S. Provisional Application No. 61/157,187, filed Mar. 3, 2009, U.S. Provisional Application No. 61/173,166, filed Apr. 27, 2009, and U.S. Provisional Application No. 61/246,070, filed Sep. 25, 2009. Each of the applications is incorporated by reference herein in its entirety for all purposes.

REFERENCE TO A SEQUENCE LISTING

This application includes an electronic sequence listing in a file named "454015-Sequence.txt", created on Nov. 25, 2014 and containing 2,792 bytes, which is hereby incorporated by reference in its entirety for all purposes.

FIELD OF THE INVENTION

The invention resides in the fields of health and beauty, cosmetic ingredients and aquaculture.

BACKGROUND OF THE INVENTION

Carbohydrates have the general molecular formula $CH_2O$, and thus were once thought to represent "hydrated carbon". However, the arrangement of atoms in carbohydrates has little to do with water molecules. Starch and cellulose are two common carbohydrates. Both are macromolecules with molecular weights in the hundreds of thousands. Both are polymers; that is, each is built from repeating units, monomers, much as a chain is built from its links.

Three common sugars share the same molecular formula: $C_6H_{12}O_6$. Because of their six carbon atoms, each is a hexose. Glucose is the immediate source of energy for cellular respiration. Galactose is a sugar in milk. Fructose is a sugar found in honey. Although all three share the same molecular formula ($C_6H_{12}O_6$), the arrangement of atoms differs in each case. Substances such as these three, which have identical molecular formulas but different structural formulas, are known as structural isomers. Glucose, galactose, and fructose are "single" sugars or monosaccharides.

Two monosaccharides can be linked together to form a "double" sugar or disaccharide. Three common disaccharides are sucrose, common table sugar (glucose+fructose); lactose, the major sugar in milk (glucose+galactose); and maltose, the product of starch digestion (glucose+glucose). Although the process of linking the two monomers is complex, the end result in each case is the loss of a hydrogen atom (H) from one of the monosaccharides and a hydroxyl group (OH) from the other. The resulting linkage between the sugars is called a glycosidic bond. The molecular formula of each of these disaccharides is $C_{12}H_{22}O_{11}=2C_6H_{12}O_6$—H2O. All sugars are very soluble in water because of their many hydroxyl groups. Although not as concentrated a fuel as fats, sugars are the most important source of energy for many cells.

SUMMARY OF THE INVENTION

The present invention relates to polysaccharides and biomass produced from microalgae or other microorganisms grown under heterotrophic conditions. Representative polysaccharides include those present in the cell wall of microalgae as well as secreted polysaccharides, or exopolysaccharides. In addition to the polysaccharides themselves, such as in an isolated, purified, or semi-purified form, the invention includes a variety of compositions containing one or more microalgal polysaccharides as disclosed herein. The compositions include nutraceutical, cosmeceutical, industrial and pharmaceutical compositions which may be used for a variety of indications and uses as described herein. Other compositions include those containing one or more microalgal polysaccharides and a suitable carrier or excipient for topical or oral administration.

The present invention also relates to microalgae for formulation in skin care products as a composition of the disclosed invention. The invention thus provides highly desirable compositions of microalgal cells that provide delivery or high value cosmeceutical ingredients such as carotenoids, polyunsaturated fatty acids, moisturizing polysaccharides, superoxide dismutase, and other components.

The invention provides the insight that various species of *Parachlorella* and *Chlorella* microalgae, when grown under heterotrophic conditions, allow for the production of biomass high in cosmeceutical/nutraceutical value as products and ingredients of a skin care forumulation. In addition, antioxidant, moisturizing polysaccharides are produced at a high level during culture and can be purified from the culture medium.

The invention further relates to methods of producing or preparing microalgal polysaccharides. In some disclosed methods, exogenous sugars are incorporated into the polysaccharides to produce polysaccharides distinct from those present in microalgae that do not incorporate exogenous sugars.

The invention further relates to methods of growing, producing and preparing microalgal biomass. In some disclosed methods, the microalgae can rapidly produce the polysaccharides when grown under heterotrophic conditions.

In another aspect, the invention relates to compositions for topical application, such as a composition for application to human skin comprising a polysaccharide isolated from cells of the genus *Parachlorella* or *Chlorella*. In some embodiments, the composition comprises a polysaccharide that is part of a microalgal cell, or a homogenate thereof. In other embodiments, the polysaccharide is contained within microalgal cells, or a homogenate thereof.

In additional embodiments, the composition is that of a cosmetic or other skin care product. Such products may contain one or more microalgal polysaccharides, or a microalgal cell homogenate, a topical carrier, and/or a preservative. In some embodiments, the carrier may be any carrier suitable for topical application, such as, but not limited to, use on human skin or human mucosal tissue. In other embodiments, the composition may contain a purified microalgal polysaccharide, such as an exopolysaccharide, and a topical carrier. Exemplary carriers include liposome formulation, biodegradable microcapsule, lotion, spray, aerosol, dusting powder, biodegradable polymer, mineral oil, liquid petroleum, white petroleum, propylene glycol, polyoxyethylene polyoxypropylene compound, emulsifying wax, sorbitan monostearate, polysorbate 60, cetyl ester wax, cetearyl alcohol, 2-octyldodecanol, benzyl alcohol, cyclomethicone, cyclopentasiloxane and water. Exemplary preservatives include diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, Germaben II, and disodium EDTA.

As a cosmeceutical, the composition may contain a microalgal polysaccharide or homogenate and other component material found in cosmetics. In some embodiments, the component material may be that of a fragrance, a colorant (e.g. black or red iron oxide, titanium dioxide and/or zinc oxide, etc.), a sunblock (e.g. titanium, zinc, etc.), and a mineral or metallic additive.

In other aspects, the invention includes methods of preparing or producing a microalgal polysaccharide. In some aspects relating to an exopolysaccharide, the invention includes methods that separate the exopolysaccharide from other molecules present in the medium used to culture exopolysaccharide producing microalgae. In some embodiments, separation includes removal of the microalgae cells from the culture medium containing the exopolysaccharide, after the microalgae has been cultured for a period of time. Of course the methods may be practiced with microalgal polysaccharides other than exopolysaccharides. In other embodiments, the methods include those where the microalgae was cultured in a bioreactor under heterotrophic conditions.

In one embodiment, the invention includes a method of producing an exopolysaccharide, wherein the method comprises culturing microalgae in a bioreactor under heterotrophic conditions, separating the microalgae cells from culture media, wherein the culture media contains the exopolysaccharide, and separating the exopolysaccharide from other molecules present in the culture media. In other embodiments, the exopolysaccharide is shed or secreted from the microalgae cells into the surrounding culture media.

The microalgae of the invention may be that of any species of microalgae that is capable of producing exopolysaccharide (high molecular weight polysaccharide that is secreted into the culture medium) when cultured under heterotrophic conditions. In some embodiments, the microalgae is from the genera *Chlorella* or *Parachlorella*. Some species in these genera have been discovered to secrete large amounts of polysaccharide into their surrounding growth media. Non-limiting examples of species within a microalgal genus of the invention include *Chlorella sorokiniana, Chlorella fusca* var. *vacuolate, Chlorella* sp., *Chlorella kessleri, Parachlorella kessleri*, and *Parachlorella beijerinckii*.

Other embodiments of the method include the separation of an exopolysaccharide from other molecules present in the culture media by tangential flow filtration. Alternatively, the methods may be practiced by separating an exopolysaccharide from other molecules present in the culture media by alcohol precipitation. Non-limiting examples of alcohols to use include ethanol, isopropanol, and methanol.

In other embodiments, a method may further comprise treating a polysaccharide or exopolysaccharide with a protease to degrade polypeptide (or proteinaceous) material attached to, or found with, the polysaccharide or exopolysaccharide. The methods may optionally comprise separating the polysaccharide or exopolysaccharide from proteins, peptides, and amino acids after protease treatment.

In other embodiments, a method of formulating a cosmeceutical composition is disclosed. As one non-limiting example, the composition may be prepared by adding separated polysaccharides, or exopolysaccharides, to homogenized microalgal cells before, during, or after homogenization. Both the polysaccharides and the microalgal cells may be from a culture of microalgae cells in suspension and under conditions allowing or permitting cell division. The culture medium containing the polysaccharides is then separated from the microalgal cells followed by (1) separation of the polysaccharides from other molecules in the medium and optionally, (2) homogenization of the cells.

Other compositions of the invention may be formulated by subjecting a culture of microalgal cells and soluble exopolysaccharide to tangential flow filtration until the composition is substantially free of salts. Alternatively, a polysaccharide is prepared after proteolysis of polypeptides present with the polysaccharide. The polysaccharide and any contaminating polypeptides may be that of a culture medium separated from microalgal cells in a culture thereof. In some embodiments, the cells are of the genus *Parachlorella*.

In a further aspect, the disclosed invention includes a composition comprising particulate polysaccharides. The polysaccharides may be from any microalgal source, and with any level of sulfation, as described herein. The composition may be sterile or substantially free of endotoxins and/or proteins in some embodiments. In other embodiments, the composition further comprises hyaluronic acid or another agent suitable or desirable for treatment of skin. The particles in some embodiments are generated by first purifying the polysaccharide away from biomass, then drying the purified polysaccharide into a film, and then homogenizing and/or grinding the film into smaller particles. In alternative embodiments the polysaccharide can be concentrated using isopropanol precipitation before or after the polysaccharide has been separated from cells.

In some embodiments, the polysaccharides are in the form of a purified material that was dried to be completely or partially insoluble in water. Preferably the purified material has been separated from cell biomass, for example as described in Example 2. In such purified form the polysaccharide is at least 50% polysaccharide by weight, and more preferably above 75% polysaccharide by weight. In some embodiments, the dried polysaccharide particles are in mixture with a non-aqueous solvent or material. In other embodiments, the dried polysaccharide particles are partially soluble such that they are from less than about 70% to less than about 1% soluble in water.

In additional embodiments, the polysaccharide particles increase in volume, or swell, on contact with water or water vapor. Thus the volume of the polysaccharide particles increases compared to its anhydrous or partially hydrated volume before exposure to the water or water vapor. In some embodiments, the particles increase in volume by an amount selected from at least about 5% to at least about 5000%.

In some embodiments, the polysaccharide compositions described herein further comprise at least one ingredient selected from the group consisting of beta carotene, lutein, astaxanthin, vitamin C, vitamin E, vitamin A, coenzyme Q10, a peptide, an acylated peptide, oil soluble α-hydroxy acid, an alkyl lactate, and salicylic acid. In some cases, the compositions comprise micronized particles containing the polysaccharide and the at least one other ingredient. In some cases, the particles are of a substantially uniform size. In some embodiments, the algal polysaccharide and the at least one ingredient have been subjected to heating, drying and homogenization to form particles comprising both algal polysaccharides and the at least one ingredient. In some cases, the particles comprising both algal polysaccharides and the at least one ingredient have been processed to a substantially uniform size.

In other embodiments, the polysaccharide compositions described herein further comprise at least one ingredient selected from the group consisting of water, sodium hyaluronate, betaine, trisodium EDTA, glycerin, blutylene glycol, amphisol K, shea butter, macadamian oil, isocetyl stearate, olive oil, PEG 150 distearate, grancil VX401, glyceryl monostearate, polyethylene, granpowder USQ, grancil PSQ, diocide and fragrance. In some cases, the compositions comprise micronized particles containing the polysaccharide and the at least one other ingredient. In some cases, the polysaccharide composition is formulated for topical administration.

The disclosed invention further includes methods for the preparation or manufacture of the dried polysaccharide particles. In some embodiments, the method comprises formulating particles of polysaccharide material into a non-aqueous material. The particles may be formed from a film of dried polysaccharide material, wherein at least a portion (or some proportion) of the film has been made completely or partially insoluble in water. Optionally, the particles are formed by homogenization of the film into particulate form.

In some cases, the film is formed by heating a suspension of polysaccharide material until all or part of the film is insoluble. The heating may be of an aqueous suspension of the material to remove water from the suspension. Of course the polysaccharide in the suspension may be from any microalgal source as described herein. Optionally, the polysaccharide in the suspension has been isolated from microalgal biomass. Optionally, the polysaccharide in the suspension has been isolated from supernatant of a culture of microalgae.

The disclosed invention thus includes a method of preparing or manufacturing a composition for topical application, such as for improving the appearance of skin. The method may comprise 1) drying an aqueous suspension of a polysaccharide isolated from microalgae to a solid film, wherein at least some proportion of the film has been made completely or partially insoluble in water; 2) homogenizing the film into particles; and optionally 3) formulating the particles into a non-aqueous material. In some embodiments, the homogenizing is via a method selected from jet milling, ball milling, Retsch® milling, pin milling and milling in a Quadro® device. Optionally, the formulating of the particles is into the non-aqueous phase of an oil-in-water emulsion, such as an emulsion suitable for topical application. The non-aqueous phase may comprise an oil suitable for topical application, such as hexadecanoic acid as a non-limiting example. In other cases, the formulating of the particles is into a carrier suitable for topical administration as described herein. In some embodiments, the particles may be relatively uniform in size or may range in size, but in many embodiments, the particles have an average size between about 400 and 0.1 microns.

The formation of a solid film may be by heating performed between about 40 and about 180 degrees Celsius. In other embodiments, the heating is performed in two parts. The first part may comprise heating a suspension, optionally aqueous, of polysaccharide material to no more than about 60 to about 100° C. for a time period sufficient to form or produce a solid film. This may be followed by a second heating of the solid film for a (second) time period sufficient to reach no more than about 148 to about 160° C. In one embodiment the first heating is in the presence of air, which may be optionally combined with the second heating (of the solid film) being in at least a partial vacuum or in a high vacuum. Of course the second heating under reduced pressure may be used independent of the first heating in the presence of air. In other embodiments the heating is done in a single step, either in the presence of air or in the presence of a partial or full vacuum.

In some alternative embodiments, a method to render the polysaccharide material insoluble is selected from chemical cross-linking, chemical dehydration through displacement of bound water by an alcohol, precipitation from solution using an alcohol or a ketone or pH, and coating of particles by microencapsulation.

In an additional aspect, the disclosed invention includes a method of topically applying a composition comprising polysaccharides in particulate form. In some embodiments, the application is to skin, such as to mammalian or human skin. Alternatively, the application is to lips or wrinkles on human skin, or by injection into skin or a skin tissue. In many embodiments, the application is to improve the appearance of skin.

In additional embodiments, a polysaccharide containing composition (optionally with polysaccharides in particulate form) may be used in a method of cosmetic enhancement. In one embodiment, a method may include injecting a polysaccharide produced by microalgae into mammalian skin. Preferably the polysaccharide is sterile and free of protein.

In further embodiments, a method to treat skin, such as mammalian or human skin, is disclosed. In some embodiments, the method is for the treatment of human facial skin or a tissue thereof. Such methods include a method of stimulating elastin synthesis in skin by applying a disclosed composition of the invention to the skin. Additional methods include a method to reduce the signs of aging or reduce the appearance of aging in human skin by applying a composition of the disclosed invention to the skin. Non-limiting examples of a sign of aging or an appearance of aging include wrinkles, such as those on the forehead or around the eyes and/or lips, and liver spots (yellowish-brown flat spots that appear as large freckles).

Additional embodiments include the use of a polysaccharide containing composition in a method of reducing the effects of ultraviolet (UV) light or radiation, such as that present in sunlight, on skin or a skin tissue. One non-limiting example is a method of shielding mammalian skin from UV light. The method may comprise applying a composition of the disclosed invention to skin or a skin tissue in an effective or sufficient amount to shield, at least in part, the skin from UV radiation. In another embodiment, a composition of the invention may be effective in the prevention of thymine dimers (TT dimers) in skin cells upon exposure to UV radiation. In an alternative embodiment, a composition of the invention may be applied in an effective or sufficient amount to treat skin that has been damaged by UV radiation. An additional non-limiting example is a method of for treating skin to reduce the risk of skin cancer induced by sunlight or UV radiation. The method may comprise applying a composition of the invention in an effective or sufficient amount to reduce the risk of UV or sunlight induced skin cancer.

An additional non-limiting example is a method of for treating skin to reduce the risk of skin cancer induced by sunlight or UV radiation that causes erythema. Erythema is redness of the skin caused by increased blood flow to the capillaries. A subject can assess the effective amount of microalgal materials sufficient to treat erythema using methods known in the art. See for example J. Invest. Dermatol., 117 (5); 1318-1321 (2001).

In addition to the above, application of a composition of the invention to human skin may be used in a method of reducing reactive oxygen species (ROS) in the skin or a skin tissue. This is based in part on the insight that the disclosed polysaccharides possess anti-oxidant activity. In some embodiments, the method is used to prevent or treat a disease or unwanted condition associated with ROS or oxidative stress. Non-limiting examples of such a disease or unwanted condition include reducing inflammation or irritation of the skin. In another embodiment, a composition of the invention may reduce inflammation by reducing lymphocyte proliferation that is associated with inflammation. In yet another embodiment, a composition of the invention may reduce inflammation by reducing the level of cytokine secretion that is associated with inflammation. In some embodiments, the polysaccharide composition comprises one or more other agents or compounds with anti-oxidant activity. In further embodiments, the method may be used to lower the level of ROS, or reduce or decrease the amount of damage caused by ROS in skin or a skin tissue. The amount of the composition may be any that is effective or sufficient to produce a desired improvement or therapeutic benefit.

In other aspects, the present invention is directed to a method of reducing fine lines and/or wrinkles on human skin, a method of inducing a feel of tightening human skin, a method of reducing transepidermal water loss in human skin, a method of moisturizing human skin, and/or a method of increasing elasticity of human skin. Each method comprises administration of a composition, as disclosed herein, to human skin in an amount and at a frequency sufficient to impart the desired characteristics. The various methods and/or compositions can be combined to provide methods or compositions suitable for imparting multiple characteristics simultaneously.

The details of additional embodiments of the invention are set forth in the accompanying drawings and the description below. Other features and advantages of the invention will be apparent from the drawings and detailed description, and from the claims.

DETAILED DESCRIPTION OF THE INVENTION

I. Definitions

Figure 1:
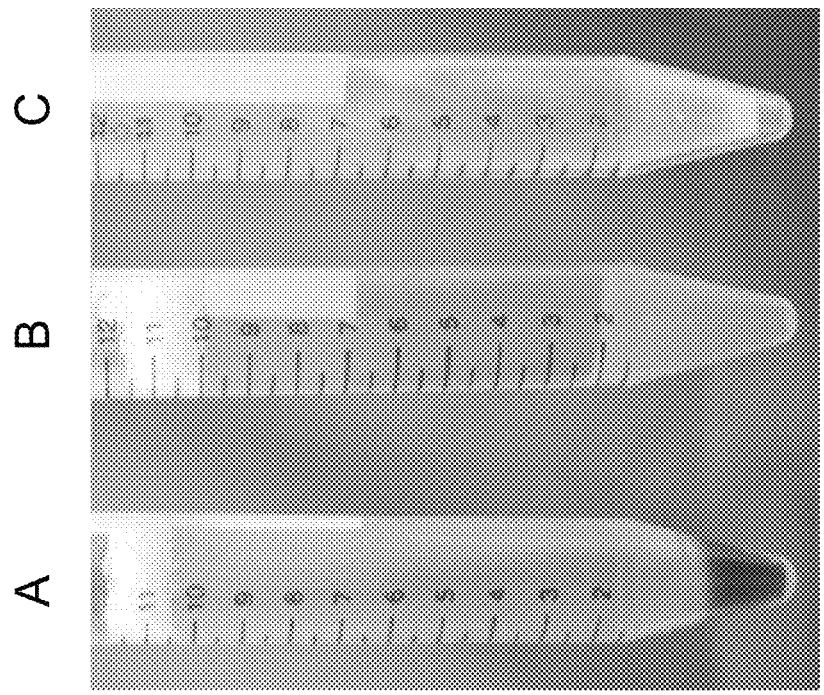
FIGS. 1A-C show purified polysaccharide beads produced from heterotrophically grown *Parachlorella beijerinckii* in media containing $NH_4$ (A) and media containing $NO_3$ (B) as a nitrogen source. 100 mg of dried polysaccharide beads (C) from each media condition was contacted with 10 ml of water and allowed to swell.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"ARA" means Arachidonic acid.

"Associates with" means, within the context of a polysaccharide binding fusion protein, one molecule binding to another molecule. Affinity and selectivity of binding can vary when a polysaccharide and a polysaccharide binding protein are in association with each other.

"Axenic" means a culture of an organism that is free from contamination by other living organisms.

The term "biomass" refers to material produced by growth and/or propagation of cells. Biomass may contain cells and/or intracellular contents as well as extracellular material. Extracellular material includes, but is not limited to, compounds secreted by a cell.

"Bioreactor" means an enclosure or partial enclosure in which cells are cultured in suspension.

"Carrier suitable for topical administration" means a compound that may be administered, together with one or more compounds of the present invention, and which does not destroy the activity thereof and is nontoxic when administered in concentrations and amounts sufficient to deliver the compound to the skin or a mucosal tissue.

The term "co-culture", and variants thereof such as "co-cultivate", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

"Combination Product" means a product that comprises at least two distinct compositions intended for human administration through distinct routes, such as a topical route and an oral route. In some embodiments the same active agent is contained in both the topical and oral components of the combination product.

"Conditions favorable to cell division" means conditions in which cells divide at least once every 72 hours.

The term "cultivated", and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor. The term does not refer to the growth or propagation of microorganisms in nature or otherwise without direct human intervention.

"DHA" means Docosahexaenoic acid.

"Endopolysaccharide" means a polysaccharide that is retained intracellularly.

"EPA" means eicosapentaenoic acid.

"Exogenously provided" describes a molecule provided to the culture media of a cell culture.

"Exopolysaccharide" means a polysaccharide that is secreted from a cell into the extracellular environment. Some exopolysaccharides are secreted by the cell and become soluble in the culture media, having lost any physical association with the cells, and are referred to as "soluble exopolysaccharides". Other exopolysaccharides remain associated with the cell wall and are referred to as "cell wall polysaccharides". Exopolysaccharides are usually a polymer of monosaccharide units and have high molecular weights, usually with average of 2 million Daltons or greater, although fragments can be smaller in size.

"Filtrate" means the portion of a tangential flow filtration sample that has passed through the filter.

"Fixed carbon source" means molecule(s) containing carbon that are present at ambient temperature and pressure in solid or liquid form.

"Food", "food composition", "food product", and "foodstuff" mean any composition intended to be or expected to be ingested by humans as a source of nutrition and/or calories. Food compositions are composed primarily of carbohydrates, fats, water and/or proteins and make up substantially all of a person's daily caloric intake.

"Glycopolymer" means a biologically produced molecule comprising at least two monosaccharides. Examples of glycopolymers include glycosylated proteins, polysaccharides, oligosaccharides, and disaccharides.

"Homogenate" means cell biomass that has been disrupted. A homogenate is not necessarily homogeneous.

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity.

As used herein, the term "lysing" refers to disrupting the cellular membrane and optionally the cell wall of a biological organism or cell sufficient to release at least some intracellular content.

A compound that can be "metabolized by cells" means a compound whose elemental components are incorporated into products endogenously produced by the cells. For example, a compound containing nitrogen that can be metabolized by cells is a compound containing at least one nitrogen atom per molecule that can be incorporated into a nitrogen-containing, endogenously produced metabolite such as an amino acid.

"Microalgae" means a eukaryotic microbial organism that contains a chloroplast, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, and can also refer to microbes such as, for example, *Volvox*, which is a simple multicellular photosynthetic microbe of two distinct cell types. "Microalgae" can also refer to cells such as *Chlorella, Parachlorella* and *Dunaliella*. "Microalgae" also includes other microbial photosynthetic organisms that exhibit cell-cell adhesion, such as *Agmenellum, Anabaena*, and *Pyrobotrys*. "Microalgae" also includes obligate heterotrophic microorganisms that have lost the ability to perform photosynthesis, such as certain dinoflagellate algae species.

The term "microalgal extract" means any component that can be extracted from microalgae. These components can include, but are not limited to, microalgal oil, proteins, lipids, carbohydrates, phospholipids, polysaccharides, macromolecules, minerals, cell wall, trace elements, carotenoids, and sterols.

The terms "microorganism" and "microbe" are used interchangeably herein to refer to microscopic unicellular organisms.

"Naturally produced" describes a compound that is produced by a wild-type organism.

"Peptide" means a polypeptide of 50 or less amino acids. In some contexts, a peptide is connected to a much larger protein as a fusion protein and is referred to as a peptide to denote its independent domain as a part of the fusion protein.

"Polysaccharide material" is a composition that contains more than one species of polysaccharide, including exopolysaccharide and optionally contaminants such as proteins, lipids, and nucleic acids, such as, for example, a microalgal cell homogenate.

"Polysaccharide" means a compound or preparation containing one or more molecules that contain at least thirty saccharide molecules covalently linked. A "polysaccharide", "endopolysaccharide" or "exopolysaccharide" can be a preparation of polymer molecules that have similar or identical repeating units but different molecular weights within the population. A "predominant species" of the polysaccharide is a polymer species that makes up at least 70% of the polysaccharide population.

"Retentate" means the portion of a tangential flow filtration sample that has not passed through the filter.

"Small molecule" means a molecule having a molecular weight of less than 2000 daltons, in some instances less than 1000 daltons, and in still other instances less than 500 daltons or less. Such molecules include, for example, heterocyclic compounds, carbocyclic compounds, sterols, amino acids, lipids, carotenoids and polyunsaturated fatty acids.

"Substantially free of protein" means compositions that are preferably of high purity and are substantially free of potentially harmful contaminants, including proteins (e.g., at least National Food (NF) grade, generally at least analytical grade, and more typically at least pharmaceutical grade). Compositions are at least 80, at least 90, at least 98%, at least 99 or at least 99.9% w/w pure of undesired contaminants such as proteins are substantially free of protein. To the extent that a given compound must be synthesized prior to use, the resulting product is typically substantially free of any potentially toxic agents, particularly any endotoxins, which may be present during the synthesis or purification process. Compositions are usually made under GMP conditions. Compositions for parenteral administration are usually sterile and substantially isotonic.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi nlm nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. In one embodiment, polysaccharides that are suitable for use in the present invention is produced by a microalgae having at least 95% 23S rRNA genomic sequence identity to SEQ ID NO: 3 or SEQ ID NO: 4.

II. General

Polysaccharides form a heterogeneous group of polymers of different length and composition. They are constructed from monosaccharide residues that are linked by glycosidic bonds. Glycosidic linkages may be located between the $C_1$ (or $C_2$) of one sugar residue and the $C_2$, $C_3$, $C_4$, $C_5$ or $C_6$ of the second residue. A branched sugar results if more than two types of linkage are present in single monosaccharide molecule.

Monosaccharides are simple sugars (saccharides) with one or more hydroxyl groups. Based on the number of carbons (e.g., 3, 4, 5, or 6) a monosaccharide is a triose, tetrose, pentose, or hexose. Pentoses and hexoses can cyclize, as the aldehyde or keto group reacts with a hydroxyl on one of the distal carbons. Examples of monosaccharides are galactose, glucose, and rhamnose.

Polysaccharides are molecules comprising a plurality of monosaccharides covalently linked to each other through glycosidic bonds. Polysaccharides consisting of a relatively small number of monosaccharide units, such as 10 or less, are sometimes referred to as oligosaccharides. The end of the polysaccharide with an anomeric carbon ($C_1$) that is not involved in a glycosidic bond is called the reducing end. A polysaccharide may consist of one monosaccharide type, known as a homopolymer, or two or more types of monosaccharides, known as a heteropolymer. Examples of homopolysaccharides are cellulose, amylose, inulin, chitin, chitosan, amylopectin, glycogen, and pectin. Amylose is a glucose polymer with $\alpha(14)$ glycosidic linkages. Amylopectin is a glucose polymer with $\alpha(14)$ linkages and branches formed by $\alpha(16)$ linkages. Examples of heteropolysaccharides are glucomannan, galactoglucomannan, xyloglucan, 4-O-methylglucuronoxylan, arabinoxylan, and 4-O-Methylglucuronoarabinoxylan.

Polysaccharides can be structurally modified both enzymatically and chemically. Examples of modifications include sulfation, phosphorylation, methylation, O-acetylation, fatty acylation, amino N-acetylation, N-sulfation, branching, and carboxyl lactonization.

Glycosaminoglycans are polysaccharides of repeating disaccharides. Within the disaccharides, the sugars tend to be modified, with acidic groups, amino groups, sulfated hydroxyl and amino groups. Glycosaminoglycans tend to be negatively charged, because of the prevalence of acidic groups. Examples of glycosaminoglycans are heparin, chondroitin, and hyaluronic acid.

Polysaccharides are produced in eukaryotes mainly in the endoplasmic reticulum (ER) and Golgi apparatus. Polysaccharide biosynthesis enzymes are usually retained in the ER, and amino acid motifs imparting ER retention have been identified (Gene. 2000 Dec. 31; 261(2):321-7). Polysaccharides are also produced by some prokaryotes, such as lactic acid bacteria.

Polysaccharides that are secreted from cells are known as exopolysaccharides. Many types of cell walls, in plants, algae, and bacteria, are composed of polysaccharides. The cell walls are formed through secretion of polysaccharides. Some species, including algae and bacteria, secrete polysaccharides that are released from the cells. In other words, these molecules are not held in association with the cells as are cell wall polysaccharides. Instead, these molecules are released from the cells. For example, cultures of some species of microalgae secrete exopolysaccharides that are suspended in the culture media.

III. Methods of Producing Polysaccharides

A. Cell Culture Methods: Microalgae

Polysaccharides can be produced by culturing microalgae. Species of microalgae for use in the invention can be identified by amplification of certain target regions of the genome. Well established methods of phylogenetic analysis, such as amplification and sequencing of ribosomal internal spacer (ITS1 and ITS2 rDNA), 23S rRNA, 18S rRNA, and other conserved genomic regions can be used by those skilled in the art to identify species that produce polysaccharides that are suitable for use in the methods disclosed herein. For examples of methods of identification and classification of algae see for example, *Genetics,* 2005 August; 170(4):1601-10 and *RNA,* 2005 April; 11(4):361-4.

Genomic DNA comparison can be used to identify suitable species of microalgae to be used in the present invention. Regions of conserved genomic DNA, such as but not limited to DNA encoding for 23S rRNA, can be amplified from microalgal species and compared to consensus sequences in order to screen for microalgal species that are taxonomically related to the preferred microalgae species that are used in the present invention. Examples of such DNA sequence comparison for species within the *Parachlorella* genus are shown below.

Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or genus of a microalgae. The use of genomic DNA comparison can be a better method of categorizing microalgae species based on their phylogenetic relationship.

In some cases, microalgae that are preferred for use in the present invention have genomic DNA sequences encoding for 23S rRNA that have at least 99%, at least 98%, at least 97%, at least 96%, at least 95%, at least 94%, at least 93%, at least 92%, at least 91%, at least 90%, at least 89%, at least 88%, at least 87%, at least 86% nucleotide identity to at least one of the sequences listed in SEQ ID NOs:3-4. In other cases, microalgae that are preferred for use in the present invention have genomic DNA sequences encoding for 23S rRNA that have at least 85%, at least 80%, at least 75%, at least 70%, at least 65%, or at least 60% nucleotide identity to at least one of the sequences listed in SEQ ID NOs:3-4.

Microalgae are preferably cultured in liquid media for polysaccharide production. Culture condition parameters can be manipulated to optimize total polysaccharide production as well as to alter the structure of polysaccharides produced by microalgae.

Microalgal culture media usually contains components such as a fixed nitrogen source, trace elements, a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

Some microalgae species can grow by utilizing a fixed carbon source such as glucose or acetate. Such microalgae can be cultured in bioreactors that do not allow light to enter. Alternatively, such microalgae can also be cultured in photobioreactors that contain the fixed carbon source and allow light to strike the cells. Such growth is known as heterotrophic growth.

Microalgae contain photosynthetic machinery capable of metabolizing photons, and transferring energy harvested from photons into fixed chemical energy sources such as monosaccharide. Glucose is a common monosaccharide produced by microalgae by metabolizing light energy and fixing carbon from carbon dioxide. Some microalgae can also grow in the absence of light on a fixed carbon source that is exogenously provided (for example see Plant Physiol. 2005 February; 137(2):460-74). In addition to being a source of chemical energy, monosaccharides such as glucose are also substrate for production of polysaccharides. The invention provides methods of producing polysaccharides with novel monosaccharide compositions. For example, microalgae is cultured in the presence of culture media that contains exogenously provided monosaccharide, such as glucose. The monosaccharide is taken up by the cell by either active or passive transport and incorporated into polysaccharide molecules produced by the cell.

In some embodiments, the fixed carbon source is one or more selected from glucose, galactose, xylose, mannose, rhamnose, N-acetylglucosamine, glycerol, floridoside, and glucuronic acid. The methods may be practiced cell growth in the presence of at least about 5.0 µM, at least about 10 µM, at least about 15.0 µM, at least about 20.0 µM, at least about 25.0 µM, at least about 30.0 µM, at least about 35.0 µM, at least about 40.0 µM, at least about 45.0 µM, at least about 50.0 µM, at least about 55.0 µM, at least about 60.0 µM, at least about 75.0 µM, at least about 80.0 µM, at least about 85.0 µM, at least about 90.0 µM, at least about 95.0 µM, at least about 100.0 µM, or at least about 150.0 µM, of one or more exogenously provided fixed carbon sources.

In some embodiments using cells of the genera *Chlorella* or *Parachlorella*, the methods include the use of approximately 1-7% glucose as a fixed carbon source wherein the cells are cultured in the dark.

B. Cell Culture Methods: Heterotrophic Growth

As an alternative to photosynthetic growth of microorganisms, as described above, some microorganisms can be cultured under heterotrophic growth conditions in which a fixed carbon source provides energy for growth and polysaccharide production.

For polysaccharide production, wild type or recombinant cells are preferably cultured or fermented in large quantities. The culturing may be in large liquid volumes, such as in suspension cultures as an example. Other examples include starting with a small culture of cells which expand into a large biomass in combination with cell growth and propagation as well as polysaccharide production. Bioreactors or steel fermentors can be used to accommodate large culture volumes. A fermentor similar those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other starch (glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp. Media suitable for heterotrophic culture of microalgal cells of the present invention is described in detail in Example 1 below. In some embodiments, the microalgal cells are from the genus *Parachlorella*. In some preferred embodiments, the microalgal cell is *Parachlorella kessleri* or *Parachlorella beijerinckii*.

A fermentor can be used to allow cells to undergo the various phases of their growth cycle. As an example, an inoculum of polysaccharide-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

In an alternate heterotrophic growth method in accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstock have been found to be inhibitory to yeast growth, and yeast cannot use the 5-carbon sugars produced from cellulosic materials (e.g., xylose from hemicellulose). By contrast, microalgae can grow on processed cellulosic material. Accordingly, the invention provides a method of culturing a microalgae in the presence of a cellulosic material and/or a 5-carbon sugar. Cellulosic materials generally include:

| Component | Percent Dry Weight |
|---|---|
| Cellulose | 40-60% |
| Hemicellulose | 20-40% |
| Lignin | 10-30% |

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

In still another alternative heterotrophic growth method in accordance with the present invention, which itself may optionally be used in combination with the methods described above, sucrose, produced by example from sugar cane or sugar beet, is used as a feedstock. Microalgae can be engineered to utilize sucrose as a carbon source. For example, expression of a sucrose transporter and a sucrose invertase allows microalgae, e.g., *Chlorella protothecoides*, to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable sucrose invertases are Genbank accession numbers CAB95010, NP_012104 and CAA06839. Examples of suitable fructokinases are Genbank accession numbers P26984, P26420 and CAA43322. Vectors for transformation of microalgae, including *Chlorella*, encoding one or more of such genes can be designed as described herein, or as described in U.S. patent application Ser. No. 12/131,783, filed Jun. 2, 2008, titled "Use of Cellulosic Materials for Cultivation of Microorganisms," and incorporated herein by reference in its entirety.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. For example, expression of a sucrose invertase with a secretion signal generates invertase activity outside the cell. See Hawkins et al., *Current Microbiology* Vol. 38 (1999), pp. 335-341 for examples of secretion signals active in *Chlorella*. Expression of such a protein, as enabled by the genetic engineering methodology disclosed herein, allows cells already capable of utilizing extracellular glucose as an energy source to utilize sucrose as an extracellular energy source.

Alternatively, a sucrose invertase can also be expressed intracellularly in cells that express a sucrose transporter, as well as in cells that express any carbohydrate transporter that allows sucrose to enter the cell.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and lipid production. In addition, the invention includes the selection and/or genetic engineering of microbes, such as microalgae, to produce microbes that are even more suitable for use in the above-described methods. For example, the microbes having a greater ability to utilize any of the above-described feedstocks for increased proliferation and/or polysaccharide production are within the scope of the invention.

C. Growth Media

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin for its culture collection of algae (UTEX).

In a particular example, a medium suitable for culturing *Chlorella protothecoides* (UTEX 31) comprises Proteose Medium. This medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM $K_2HPO_4$, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use.

In another particular example, a medium suitable for the heterotrophic culture of various *Parachlorella* species is also based off of Bristol Medium. This medium is suitable for axenic cultures and contains the following: 15 mM $NaNO_3$, 0.17 mM $CaCl_2.2H_2O$, 0.97 mM $MgSO_4.7H_2O$, 0.43 mM $K_2HPO_4$, 1.28 mM $KH_2PO_4$, and 0.43 mM NaCl and 4 g/L yeast extract plus trace minerals and vitamins in an aqueous solution. The solution is covered and autoclaved, and then stored at a refrigerated temperature prior to use.

Another medium that is suitable for heterotrophic culture of microalgae for polysaccharide production contains the following: K2HPO4 (0.14 g/L); NaH2PO4 (0.11 g/L); MgSO4.7H2O (0.37 g/L); (NH4)2SO4 (1.00 g/L); CaCl2.2H2O (0.03 g/L); yeast extract (4.00 g/L) and citric acid (0.25 g/L) plus trace minerals and vitamins in deionized water.

Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic).

D. Non-Microalgal Polysaccharide Production

Organisms besides microalgae can be used to produce polysaccharides, such as lactic acid bacteria (see for example Stinglee, F., Molecular Microbiology (1999) 32(6), 1287-1295; Ruas_Madiedo, P., J. Dairy Sci. 88:843-856 (2005); Laws, A., Biotechnology Advances 19 (2001) 597-625; Xanthan gum bacteria: Pollock, T J., J. Ind. Microbiol Biotechnol., 1997 August; 19(2):92-7; Becker, A., Appl. Micrbiol. Bioltechnol. 1998 August; 50(2):92-7; Garcia-Ochoa, F., Biotechnology Advances 18 (2000) 549-579, seaweed: Talarico, L B., et al., Antiviral Research 66 (2005) 103-110; Dussealt, J., et al., J Biomed Mater Res A., (2005) November 1; Melo, F. R., J Biol Chem 279:20824-35 (2004)).

E. Ex Vivo Methods

Microalgae and other organisms can be manipulated to produce polysaccharide molecules that are not naturally produced by methods such as feeding cells with monosaccharides that are not produced by the cells (Nature. 2004 Aug. 19; 430(7002):873-7).

F. In Vitro Methods

Polysaccharides can be altered by enzymatic and chemical modification. For example, carbohydrate modifying enzymes can be added to a preparation of polysaccharide and allowed to catalyze reactions that alter the structure of the polysaccharide. Chemical methods can be used to, for example, modify the sulfation pattern of a polysaccharide (see for example Carbohydr. Polym. 63:75-80 (2000); Pomin V H., Glycobiology. 2005 December; 15(12):1376-85; Naggi A., Semin Thromb Hemost. 2001 October; 27(5): 437-43 Review; Habuchi, O., Glycobiology. 1996 January; 6(1); 51-7; Chen, J., J. Biol. Chem. In press; Geresh., S et al., J. Biochem. Biophys. Methods 50 (2002) 179-187.).

G. Polysaccharide Purification Methods

Exopolysaccharides can be purified from microalgal cultures by various methods, including those disclosed herein.

1. Precipitation

For example, polysaccharides can be precipitated by adding compounds such as cetylpyridinium chloride, isopropanol, ethanol, or methanol to an aqueous solution containing a polysaccharide in solution. Pellets or fibers of precipitated polysaccharide can be washed and resuspended in water, buffers such as phosphate buffered saline or Tris, or other aqueous solutions (see for example Farias, W. R. L., et al., J. Biol. Chem. (2000) 275; (38)29299-29307; U.S. Pat. Nos. 6,342,367; 6,969,705).

2. Dialysis

Polysaccharides can also be dialyzed to remove excess salt and other small molecules (see for example Gloaguen, V., et al., Carbohydr Res. 2004 Jan. 2; 339(1):97-103; Microbiol Immunol. 2000; 44(5):395-400.).

3. Tangential Flow Filtration

Filtration can be used to concentrate polysaccharide and remove salts. For example, tangential flow filtration (TFF), also known as cross-flow filtration, can be used)). For a preferred filtration method see Geresh, Carb. Polym. 50; 183-189 (2002), which discusses use of a MaxCell A/G technologies 0.45 uM hollow fiber filter. Also see for example Millipore Pellicon® devices, used with 100 kD, 300 kD, 1000 kD (catalog number P2C01MC01), 0.1 uM (catalog number P2VVPPV01), 0.22 uM (catalog number P2GVPPV01), and 0.45 uM membranes (catalog number P2HVMPV01). It is preferred that the polysaccharides do not pass through the filter at a significant level. It is also preferred that polysaccharides do not adhere to the filter material. TFF can also be performed using hollow fiber filtration systems.

Non-limiting examples of tangential flow filtration include use of a filter with a pore size of at least about 0.1 micrometer, at least about 0.12 micrometer, at least about 0.14 micrometer, at least about 0.16 micrometer, at least about 0.18 micrometer, at least about 0.2 micrometer, at least about 0.22 micrometer, or at least about 0.45 micrometer. Preferred pore sizes of TFF allow contaminants to pass through but not polysaccharide molecules.

4. Ion Exchange Chromatography

Anionic polysaccharides can be purified by anion exchange chromatography. (Jacobsson, I., Biochem J. 1979 Apr. 1; 179(1):77-89; Karamanos, N K., Eur J Biochem. 1992 Mar. 1; 204(2):553-60).

5. Protease Treatment

Polysaccharides can be treated with proteases to degrade contaminating proteins. In some instances the contaminating proteins are attached, either covalently or noncovalently to polysaccharides. In other instances the polysaccharide molecules are in a preparation that also contains proteins. Proteases can be added to polysaccharide preparations containing proteins to degrade proteins (for example, the protease from *Streptomyces griseus* can be used (SigmaAldrich catalog number P5147). After digestion, the polysaccharide is preferably purified from residual proteins, peptide fragments, and amino acids. This purification can be accomplished, for example, by methods listed above such as dialysis, filtration, and precipitation.

Heat treatment can also be used to eliminate proteins in polysaccharide preparations (see for example Biotechnol Lett. 2005 January; 27(1):13-8; FEMS Immunol Med Microbiol. 2004 Oct. 1; 42(2):155-66; Carbohydr Res. 2000 Sep. 8; 328(2):199-207; J Biomed Mater Res. 1999; 48(2): 111-6; Carbohydr Res. 1990 Oct. 15; 207(1):101-20).

The invention thus includes production of an exopolysaccharide comprising separating the exopolysaccharide from contaminants after proteins attached to the exopolysaccharide have been degraded or destroyed. The proteins may be those attached to the exopolysaccharide during culture of a microalgal cell in media, which is first separated from the cells prior to proteolysis or protease treatment. The cells may be those of the genus *Parachlorella* as a non-limiting example.

In one non-limiting example, a method of producing an exopolysaccharide is provided wherein the method comprises culturing cells of the genus *Parachlorella*; separating cells from culture media; destroying protein attached to the exopolysaccharide present in the culture media; and separating the exopolysaccharide from contaminants. In some methods, the contaminant(s) are selected from amino acids, peptides, proteases, protein fragments, and salts. In other methods, the contaminant is selected from NaCl, $MgSO_4$, $MgCl_2$, $CaCl_2$, $KNO_3$, $KH_2PO_4$, $NaHCO_3$, Tris, $ZnCl_2$, $H_3BO_3$, $CoCl_2$, $CuCl_2$, $MnCl_2$, $(NH_4)_6Mo_7O_{24}$, FeCl3 and EDTA.

6. Whole Cell Extraction

Intracellular polysaccharides and cell wall polysaccharides can be purified from whole cell mass (see form example U.S. Pat. Nos. 4,992,540; 4,810,646; J Sietsma J H., et al., Gen Microbiol. 1981 July; 125(1):209-12; Fleet G H, Manners D J., J Gen Microbiol. 1976 May; 94(1):180-92).

H. Drying Methods

After purification of methods such as those above, polysaccharides can be dried using methods such as lyophilization and heat drying (see for example Shastry, S., Brazilian Journal of Microbiology (2005) 36:57-62; Matthews K H., Int J Pharm. 2005 Jan. 31; 289(1-2):51-62. Epub 2004 Dec. 30; Gloaguen, V., et al., Carbohydr Res. 2004 Jan. 2; 339(1):97-103).

Tray dryers accept moist solid on trays. Hot air (or nitrogen) can be circulated to dry. Shelf dryers can also employ reduced (below atmospheric at sea level, such as at about 25 in Hg or less) pressure or vacuum to dry at room temperature when products are temperature sensitive and are similar to a freeze-drier but less costly to use and can be easily scaled-up. In some embodiments drying in oven tray dryers is performed under vacuum.

Spray dryers are relatively simple in operation, which accept feed in fluid state and convert it into a dried particulate form by spraying the fluid into a hot drying medium.

Rotary dryers operate by continuously feeding wet material, which is dried by contact with heated air, while being transported along the interior of a rotating cylinder, with the rotating shell acting as the conveying device and stirrer.

Spin flash dryers are used for drying of wet cake, slurry, or paste which is normally difficult to dry in other dryers. The material is fed by a screw feeder through a variable speed drive into the vertical drying chamber where it is heated by air and at the same time disintegrated by a specially designed disintegrator. The heating of air may be direct or indirect depending upon the application. The dry powder is collected through a cyclone separator/bag filter or with a combination of both.

I. Microalgae Homogenization Methods

A pressure disrupter pumps a slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method is applied mainly for the release of intracellular molecules. According to Hetherington et al., cell disruption (and consequently the rate of protein release) is a first-order process, described by the relation: $\log[Rm/(Rm-R)]=K\ N\ P72.9$. R is the amount of soluble protein; Rm is the maximum amount of soluble protein K is the temperature dependent rate constant; N is the number of passes through the homogenizer (which represents the residence time). P is the operating pressure.

In a ball mill, cells are agitated in suspension with small abrasive particles. Cells break because of shear forces, grinding between beads, and collisions with beads. The beads disrupt the cells to release biomolecules. The kinetics of biomolecule release by this method is also a first-order process.

Another widely applied method is the cell lysis with high frequency sound that is produced electronically and transported through a metallic tip to an appropriately concentrated cellular suspension, ie: sonication. The concept of ultrasonic disruption is based on the creation of cavities in cell suspension. Homogenization can also be performed with a Microfluidizer® device (such as the M-110Y Microfluidizer® model, Microfluidics Inc., Newton, Mass.).

Blending (high speed or Waring), the french press, or even centrifugation in the case of weak cell walls, also disrupt the cells by using the same concepts.

Cells can also be ground after drying in devices such as a colloid mill or a jet air mill. The jet air mill uses compressed high pressure air to grind material into particles of about 10 µm or less.

Because the percentage of polysaccharide as a function of the dry weight of a microalgae cell can frequently be in excess of 50%, microalgae cell homogenates can be considered partially purified polysaccharide compositions. Purified or isolated polysaccharide compositions contain less than 20% and preferably, less than 10% proteins, nucleic acids, intra-cellular components such as other polysaccharides found intracellularly that are commonly found in microalgae cell homogenate. Cell disruption aids in increasing the amount of solvent-accessible polysaccharide by breaking apart cell walls that are largely composed of polysaccharide.

Homogenization as described herein can increase the amount of solvent-available polysaccharide significantly. For example, homogenization can increase the amount of solvent-available polysaccharide by at least a factor of 0.25, at least a factor of 0.5, at least a factor of 1, at least a factor of 2, at least a factor of 3, at least a factor of 4, at least a factor of 5, at least a factor of 8, at least a factor of 10, at least a factor of 15, at least a factor of 20, at least a factor of 25, and at least a factor of 30 or more compared to the amount of solvent-available polysaccharide in an identical or similar quantity of non-homogenized cells of the same type. One way of determining a quantity of cells sufficient to generate a given quantity of homogenate is to measure the amount of a compound in the homogenate and calculate the gram quantity of cells required to generate this amount of the compound using known data for the amount of the compound per gram mass of cells. The quantity of many such compounds per gram of particular microalgae cells are know. Given a certain quantity of a compound in a composition, the skilled artisan can determine the number of grams of intact cells necessary to generate the observed amount of the compound. The number of grams of microalgae cells present in the composition can then be used to determine if the composition contains at least a certain amount of solvent-available polysaccharide sufficient to indicate whether or not the composition contains homogenized cells, such as for example five times the amount of solvent-available polysaccharide present in a similar or identical quantity of unhomogenized cells.

J. Decolorization

In some cases, heterotrophically produced microalgal polysaccharides or extracts have pigment or coloration as a by-product of the fermentation process. Such pigment or coloration may be undesirable for cosmetic or nutraceutical formulation. In some cases, pigment or coloration may stain human skin when applied as part of a skin care formulation. In other cases, pigment or coloration may be visually unappealing to end-user consumers as part of a skin care or cosmetic composition. In such cases, a decolorization step to remove the pigment or coloration in the microalgal homogenate/extract or polysaccharide may be performed. Many methods of decolorization are known in the art and may be suitable for use in the present invention. Such methods include, but are not limited to, bleaching, solvent treatment, treatment with activated carbon or charcoal or other pourous material such as clay, acid rinse, alcohol rinse, washing with high salt solutions and enzyme treatment.

K. Analysis Methods

Assays for detecting polysaccharides can be used to quantitate starting polysaccharide concentration, measure yield during purification, calculate density of secreted polysaccharide, measure polysaccharide concentration in a finished product, and other purposes.

The phenol: sulfuric acid assay detects carbohydrates (see Hellebust, Handbook of Phycological Methods, Cambridge University Press, 1978; and Cuesta G., et al., J Microbiol Methods. 2003 January; 52(1):69-73). The 1,6 dimethylmethylene blue assay detects anionic polysaccharides. (see for example Braz J Med Biol Res. 1999 May; 32(5):545-50; Clin Chem. 1986 November; 32(11):2073-6).

Polysaccharides can also be analyzed through methods such as HPLC, size exclusion chromatography, and anion exchange chromatography (see for example Prosky L, Asp N, Schweizer T F, DeVries J W & Furda I (1988) Determination of insoluble, soluble and total dietary fiber in food and food products: Interlaboratory study. Journal of the Association of Official Analytical Chemists 71, 1017±1023; Int J Biol Macromol. 2003 November; 33(1-3):9-18)

Polysaccharides can also be detected using gel electrophoresis (see for example Anal Biochem. 2003 Oct. 15; 321(2):174-82; Anal Biochem. 2002 Jan. 1; 300(1):53-68).

Monosaccharide analysis of polysaccharides can be performed by combined gas chromatography/mass spectrometry (GC/MS) of the per-O-trimethylsilyl (TMS) derivatives of the monosaccharide methyl glycosides produced from the sample by acidic methanolysis (see Merkle and Poppe (1994) Methods Enzymol. 230: 1-15; York, et al. (1985) Methods Enzymol. 118:3-40).

The determination of protein concentration may be by use of any known procedure, such as the Lowry assay, the Biuret assay, the Bradford assay, or the bicinchoninic acid (BCA) assay. As a non-limiting example, the BCA assay is based on the formation of a $Cu^{2+}$-protein complex under alkaline conditions. The $Cu^{2+}$ is then reduced to $Cu^{1+}$ where the amount of protein present is proportional to the amount reduction. The reduction has been shown to be mediated by amino acids such as cysteine, cystine, tryptophan, and tyrosine as well as the peptide bond. The result of the assay is a purple-blue complex with $Cu^{1+}$ under alkaline conditions. The color complex is stable, even in the presence of other components possibly present with the proteins, such as detergents. The amount of reduction can be monitored by absorbance at 562 nm. The BCA assay is sensitive and accurate over a broad range of protein concentrations.

IV. Compositions

Compositions of the invention include a microalgal polysaccharide or homogenate as described herein. In embodiments relating to polysaccharides, including exopolysaccharides, the composition may comprise a homogenous or a heterogeneous population of polysaccharide molecules, including sulfated polysaccharides as non-limiting embodiments. Non-limiting examples of homogenous populations include those containing a single type of polysaccharide molecule, such as that with the same structure and molecular weight. Non-limiting examples of heterogeneous populations include those containing more than one type of polysaccharide molecule, such as a mixture of polysaccharides having a molecular weight (MW) within a range or a MW above or below a MW value. In some cases, the polysaccharide has an average molecular weight around 2 million Daltons. For example, exopolysaccharide from microalgae from the genus *Parachlorella* is typically about 2 million Daltons. Of course a polysaccharide containing composition of the invention may be optionally protease treated, or reduced in the amount of protein, as described above.

In some embodiments, a composition of the invention may comprise one or more polysaccharides produced by microalgae that have not been recombinantly modified. The microalgae may be those which are naturally occurring or those which have been maintained in culture in the absence of alteration by recombinant DNA techniques or genetic engineering.

In other embodiments, the polysaccharides are those from modified microalgae, such as, but not limited to, microalgae modified by recombinant techniques. Non-limiting examples of such techniques include introduction and/or expression of an exogenous nucleic acid sequence encoding a gene product; genetic manipulation to decrease or inhibit expression of an endogenous microalgal gene product; and/or genetic manipulation to increase expression of an endogenous microalgal gene product. The invention contemplates recombinant modification of the various microalgae species described herein. In some embodiments, the microalgae is from the genus *Parachlorella*.

In some embodiments, some microalgae grown under different heterotrophic conditions may produce polysaccharides that are different in their monosaccharide composition. Embodiments include altering the nitrogen source, such as in a non-limiting example, using $NH_4$ instead of $NO_3$, may change the monosaccharide composition of the polysaccharide that is produced by the microalgae.

In some embodiments, the microalgae is of the genus *Parachlorella*, as a non-limiting example. In some cases, the cell is selected from *Parachlorella kessleri*. and *Parachlorella beijerinckii*. Embodiments include those wherein the polysaccharide is enriched for at least one monosaccharide compared to an endogenous polysaccharide produced by a non-transgenic cell of the same species. The monosaccharide may be selected from Arabinose, Fructose, Galactose, Glucose, Mannose, Xylose, Glucuronic acid, Glucosamine, Galactosamine, Rhamnose and N-acetyl glucosamine.

In some aspects, the invention includes a novel microalgal polysaccharide, such as from the microalgae of the genus *Parachlorella*, comprising detectable amounts of rhamnose, xylose, mannose, galactose and glucose. In some embodiments, the microalgal polysaccharide further comprises detectable amounts of glucuronic acid. In some embodiments, the microalgae have been nutritionally modified resulting in a different profile of monosaccharides in the microalgal polysaccharide.

In some embodiments, the microalgal polysaccharide comprises 15-55 mole percent rhamnose; 3-30 mole % xylose; 1-25 mole percent mannose; 1-45 mole % galactose; and 0.5-10 mole % glucose. In other embodiments, the microalgal polysaccharide further comprises about 22 mole percent arabinose. In other embodiments, the microalgal polysaccharide further comprises 0.1-15 mole percent glucuronic acid.

In other embodiments, the microalgal polysaccharide comprises 17-35 mole percent rhamnose; 4-13 mole percent xylose; 8-16 mole percent mannose; 30-43 mole percent galactose; and 2.5-8 mole percent glucose.

In some embodiments, the microalgal polysaccharide is from *Parachlorella kessleri* and comprises about 52.8 mole percent rhamnose; about 26.6 mole percent xylose; about 9.8 mole percent glucuronic acid; about 2.2 mole percent mannose; about 7.5 mole percent galactose; and about 1.0 mole percent glucose. In other embodiments, the microalgal polysaccharide from *Parachlorella kessleri* comprises about 33.0 mole percent rhamnose; about 12.9 mole percent xylose; about 3.9 mole percent glucuronic acid; about 15.4 mole percent mannose; about 31.8 mole percent galactose; about 2.9 mole percent glucose.

In other embodiments, the microalgal polysaccharide is from *Parachlorella beijerinckii* and comprises about 50.1 mole percent rhamnose; about 31.2 mole percent xylose; about 11.5 mole percent glucuronic acid; about 1.4 mole percent mannose; about 4.3 mole percent galactose; and about 1.4 mole percent glucose. In other embodiments, the microalgal polysaccharide from *Parachlorella beijerinckii* comprises 27.0-31.4 mole percent rhamnose; 11.4-16.3 mole percent xylose; 0-5.4 mole percent glucuronic acid; 18.5-18.8 mole percent mannose; 30.5-35.2 mole percent galactose; 2.7-2.9 mole percent glucose.

In still other embodiments, the microalgal polysaccharide is from *Chlorella sorokiniana* and comprises about 21.6 mole percent arabinose; about 17.3 mole percent rhamnose; about 4.0 mole percent xylose; about 0.3 mole percent glucuronic acid; about 7.1 mole percent mannose; about 42.0 mole percent galactose; and about 7.8 mole percent glucose.

V. Cosmeceutical Compositions and Topical Application

A. General

Compositions, comprising polysaccharides, whole cell extracts, or mixtures of polysaccharides and whole cell extracts, are provided for topical application or non-systemic administration. The polysaccharide may be any one or more of the microalgal polysaccharides disclosed herein, including those produced by a species, or a combination of two or more species. Similarly, a whole cell extract may be that prepared from a microalgal species, or a combination of two or more species. In some embodiments, polysaccharides, such as exopolysaccharides, and cell extracts from microalgae of the genera *Chlorella* or *Parachlorella* are used in the practice of the invention. A composition of the invention may comprise from between about 0.001% and about 100%, about 0.01% and about 90%, about 0.1% and about 80%, about 1% and about 70%, about 2% and about 60%, about 4% and about 50%, about 6% and about 40%, about 7% and about 30%, about 8% and about 20%, or about 10% polysaccharide, and/or cell extract, by weight.

In a preferred embodiment, a composition of the invention may comprise about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19% or about 0.20% polysaccharide by weight. In another preferred embodiment, a composition of the invention may comprise from about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1%, about 1.5%, about 2%, about 2.5%, about 3%, about 3.5%, about 4%, about 4.5%, about 5%, about 5.5%, about 6.0%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 65%, about 70%, about 75%, about 80%, about 85%, about 90%, about 95% or about 100% polysaccharide by weight.

In other embodiments, the composition comprises a carrier suitable for topical administration and/or a preservative suitable for topical administration; of the genus *Parachlorella* or *Chlorella*. In further embodiments, the carrier is suitable for topical administration to humans, such as to human skin or a skin tissue.

In alternative embodiments, a composition for application to human skin may comprise a polysaccharide isolated from cells of the genus *Parachlorella* or *Chlorella*. Such a composition may further comprise a carrier and/or preservative suitable for topical administration as described herein. In some cases, the polysaccharide of the composition contains no more than about 10% protein by weight. In other embodiments, the polysaccharide contains no more than about 5%, no more than about 2%, or no more than about 1% protein by weight. The polysaccharide may also be essentially, or completely, free of protein, as detectable by assay methods as described herein after treatment to remove protein.

In further embodiments, the polysaccharide may comprise a molar amount of glucose that is at least about 5%, at least about 10%, at least about 15%, at least about 20%, at least about 25%, at least about 30%, at least about 35%, at least about 40%, at least about 45% at least about 50%, or at least about 60%, of the molar amount of galactose. Alternatively, the molar amount of glucose in the polysaccharide is greater than the molar amount of galactose. In additional embodiments, the polysaccharide contains less than a 0.1%, or less than a 0.01%, molar amount of at least one monosaccharide selected from the group consisting of arabinose, galacturonic acid, fucose, and N-acetyl glucosamine. Optionally, the polysaccharide contains less than a 0.1%, or less than a 0.01%, molar amount of each of arabinose, rhamnose, fucose, and N-acetyl glucosamine.

In yet further embodiments, the polysaccharides are sulfated exopolysaccharides containing at least about 0.05% sulfur, at least about 0.1% sulfur, at least about 0.15% sulfur, at least about 0.2% sulfur, at least about 0.25% sulfur, at least about 0.3% sulfur, at least about 0.35% sulfur, at least about 0.4% sulfur, at least about 0.45% sulfur, at least about 0.5% sulfur, at least about 0.55% sulfur, at least about 0.6% sulfur, at least about 0.65% sulfur, at least about 0.07% sulfur, at least about 0.75% sulfur, at least 0.8% sulfur, at least 0.9% sulfur, at least 1% sulfur, at least 2% sulfur, at least 3% sulfur, at least 4% sulfur, at least 5% sulfur, at least 6% sulfur, at least 7% sulfur, at least 8% sulfur, at least 9% sulfur, or at least 10% sulfur by weight of the polysaccharide. The amount or level of sulfation in the polysaccharides may be analyzed and compared to the amount of sulfates used to culture the microalgae. Thus, the amount or level of sulfation in the polysaccharides of cells grown at less than 50 mM, at about 100 mM, about 200 mM, about 300 mM, about 400 mM, about 500 mM, about 600 mM, or about 700 mM or higher, sulfate ($SO_4^{2-}$) may be determined by routine and repetitive methods disclosed herein. The amount or level of sulfur by weight in the polysaccharides of a sample of cells or cell material may be determined without knowledge of the amount of sulfate used to culture the cells.

In another embodiment, the polysaccharides are subjected to chemical sulfation in order to produce a polysaccharide with a high degree of sulfation. Chemical sulfation processes are well known in the art and are suitable for use in the present invention. For example, U.S. Pat. No. 2,599,564 describes methods of chemical sulfation using chlorosulfonic acid and pyridine. U.S. Pat. No. 2,755,275 describes a method of sulfating chitin which uses chlorosulfonic acid or sulfur trioxide as the sulfating agent in an inert solvent such as dichloroethane or other liquid halogenated alkanes. U.S. Pat. No. 4,814,437 describes methods of generating sulfated polysaccharides using pyridine-chlorosulfonic acid, but with a pre-treatment with a reducing agent in order to minimize pyridinium substituents during the preparation of sulfated polysaccharides. This method was shown to achieve between 13%-18% sulfur content in the polysaccharide. In one embodiment the invention comprises polysaccharides from *Parachlorella* or *Chlorella* with over 2%, over 5% and over 10% sulfur by weight achieved through the methods of chemical sulfation describerd herein.

As a further alternative, a composition for topical application to human skin may comprise microalgal cells. The cells may be those of genus *Parachlorella* or *Chlorella* or any other species or strain as disclosed herein. Optionally, the composition further comprises a carrier and/or preservative suitable for topical administration as described herein. In alternative embodiments, the cells are homogenized (such as by methods described herein) to generate or form a microalgal cell homogenate. In some cases, the cells or homogenate thereof, and therefore the composition, is essentially free of red and/or green coloration.

In further embodiments, the disclosed invention includes a composition comprising particulate polysaccharides, such as microbeads or nanobeads comprising a disclosed polysaccharide. In some embodiments the polysaccharide particles are referred to as Alguronic™ Acid microspheres. The composition may be for improving the appearance of skin, such as human skin. The polysaccharides may have any level of sulfation described herein. The composition may be sterile and/or non-pyrogenic and optionally substantially free of endotoxins and/or proteins. In other embodiments, the composition further comprises hyaluronic acid or another agent suitable or desirable for treatment of skin. Non-limiting examples of such an agent include aloe vera, urea, alpha hydroxyl acid, vitamin E, glycyrrhizinic acid, methylsulfonylmethane (MSM), and collagen.

In some embodiments, the composition comprises an algal polysaccharide, wherein the polysaccharide: (a) has been made completely or partially insoluble in water through drying; and (b) has been homogenized or otherwise milled or disrupted to generate particles.

The polysaccharide may of course be that of a variety of microalgal cells, such as those of the genera *Parachlorella* or *Chlorella*. In some cases, the polysaccharide is contained in a non-aqueous material. As non-limiting examples, the material may be contained in an oil suitable for topical administration, with hexadecanoic acid or oil that is contained in an emulsion as representative examples. In one embodiment, the particulate polysaccharides from a species of the genus *Parachlorella* are formulated in at least one of the following compounds: Ceraphyl (Ethylhexyl Palmitate), Aerosil (silica dimethyl silylate), butylene glycol, and a preservative such as diocide, dowicil 200, and methyl paraben. In some embodiments the concentrations of formulated particulate polysaccharides from a species of the genus *Parachlorella* are between 50-97% Ceraphyl (Ethylhexyl Palmitate), 1-5% Aerosil (silica dimethyl silylate), 0.1-3 butylene glycol, and 0.1-3% of a preservative such as diocide, dowicil 200, and methyl paraben. The composition may also comprise a carrier and/or preservative suitable for topical administration. The composition may also be substantially free of endotoxins and/or protein as well as sterile and/or non-pyrogenic. In further embodiments, the polysaccharide is encapsulated by a timed-release coating, such as one suitable for topical application to human skin.

In another embodiment, the polysaccharides from a species of the genus *Parachlorella* are formulated with at least one of the following compounds: cyclopentasiloxane, vinyl dimethicone crosspolymer, polymethyl methacrylate, isodeocecane, disteardimonium hectorite, phytoene, phytofluene, vitamin C, vitamin E. The composition may also comprise a carrier and/or preservative suitable for topical administration. The composition may also comprise a fragrance. The composition may also be substantially free of endotoxins and/or protein as well as sterile and/or non-pyrogenic. In further embodiments, the polysaccharide is encapsulated by a timed-release coating, such as one suitable for topical application to human skin.

In yet another embodiment, the polysaccharides from a species of the genus *Parachlorella* or *Chlorella* are formulated with at least one of the following compounds: water, sodium hyaluronate, betaine, trisodium EDTA, glycerin, butylene glycol, amphisol K, shea butter, macadamian oil, isocetyl stearate, olive oil, PEG 150 distearate, grancil VX401, glyceryl monostearate, polyethylene, granpowder USQ, grancil PSQ, diocide and fragrance.

Optionally, the composition is prepared by a manufacturing or preparation method as described herein, such as a method disclosed in the following Methods of Formulation section. In some cases, the composition comprises a polysaccharide that is partially or completely insoluble in water, such as by heating an aqueous suspension of the polysaccharide, thereby removing water from the suspension. The polysaccharide particulates may be partially soluble such that they are less than about 70%, less than about 60%, less than about 50%, less than about 40%, less than about 30%, less than about 20%, less than about 10%, less than about 5%, or less than about 2% soluble in water.

In other embodiments, the polysaccharide has been made partially or completely insoluble by a method selected from the group consisting of chemical cross-linking, chemical dehydration through displacement of bound water by an alcohol, precipitation from solution using an alcohol or a ketone or pH, and coating of particles by microencapsulation. Non-limiting examples of these methods are known to the skilled person and may be used in the practice of the invention. For examples, see Biomacromolecules. 2005 November-December; 6(6):3202-8; Arterioscler Thromb Vasc Biol. 2004 March; 24(3):613-7; J Biomed Mater Res. 2001 Sep. 15; 56(4):478-86; Dalton Trans. 2004 Sep. 7; (17):2621-34. Epub 2004 Jul. 28; Biomacromolecules. 2004 January-February; 5(1):126-36; Contraception. 2002 August; 66(2):137-40; Biomacromolecules. 2006 May; 7(5):1471-80; Biopolymers. 1999 September; 50(3):227-37; Biomaterials. 2003 May; 24(12):2083-96; Int J Pharm. 2003 Nov. 28; 267(1-2):13-25; Med Biol Eng Comput. 1998 January; 36(1):129-34 and Reprod Fertil Dev. 2002; 14(5-6):307-14. A representative example is chemical cross-linking to a pharmaceutically or cosmetically acceptable insoluble solid phase material, such as a polymer, microbead, or nanobead. The insoluble material need not precipitate when in a solution but includes a material that remains in suspension when in solution. Dehydration or precipitation with alcohol may be practiced with any alcohol suitable for pharmaceutical or cosmetic use. Non-limiting examples include ethanol or a fatty alcohol such as cetyl, stearyl, cetearyl, or lanolin alcohol. A non-limiting method of microencapsulating a cosmetic is described in U.S. Pat. No. 4,752,496.

The use of a disclosed method of the invention also includes milling of dried polysaccharide material (such as a film) into particles by any suitable method. Non-limiting examples of such methods are disclosed herein, and they produce particles with an average size that may range between about 400 and about 0.1 microns.

In some embodiments, the composition comprises polysaccharide particles that increase in volume on contact with water compared to their anhydrous or partially hydrated volume. In some embodiments, the particles increase in volume by an amount selected from at least about 5%, at least about 25%, at least about 50%, at least about 100%, at least about 200%, at least about 300%, by at least about 500%, at least about 1000%, or at least about 5000%.

When the polysaccharide particles come into contact with water, the water/polysaccharide solution will increase in viscosity. In some embodiments, dried, purified microalgal polysaccharides that are resuspended in water at a 1% w/v concentration have a viscosity of between 500 cP and 1000 cP. In other embodiments, dried, purified microalgal polysaccharides that are resuspended in water at a 1% w/v concentration have a viscosity of greater than 1000 cP.

Topical compositions are usually formulated with a carrier, such as in an ointment or a cream, and may optionally include a fragrance. One non-limiting class of topical compositions is that of cosmeceuticals. Other non-limiting examples of topical formulations include gels, solutions, impregnated bandages, liposomes, or biodegradable microcapsules as well as lotions, sprays, aerosols, suspensions, dusting powder, impregnated bandages and dressings, biodegradable polymers, and artificial skin. Another non-limiting example of a topical formulation is that of an ophthalmic preparation. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water.

In some embodiments, the polysaccharides contain fucose moieties. In other embodiments, the polysaccharides are sulfated, such as exopolysaccharides from microalgae of the genus *Parachlorella*. In some embodiments, the polysaccharides will be those from a *Parachlorella* species, such as one that has been subject to genetic and/or nutritional manipulation to produce polysaccharides with altered monosaccharide content and/or altered sulfation.

In additional embodiments, a composition of the invention comprises a microalgal cell homogenate and a topical carrier.

B. Methods of Formulation

Polysaccharide compositions for topical application can be formulated by first preparing a purified preparation of polysaccharide. As a non-limiting example, the polysaccharide from aqueous growth media is precipitated with an alcohol, resuspended in a dilute buffer, and mixed with a carrier suitable for application to human skin or mucosal tissue, including the vaginal canal. Alternatively, the polysaccharide can be purified from growth media and concentrated by tangential flow filtration or other filtration methods, and formulated as described above. Intracellular polysaccharides can be also formulated in a similar or identical manner after purification from other cellular components.

As a non-limiting example, the invention includes a method of formulating a cosmeceutical composition, said method comprising culturing microalgal cells in suspension under conditions to allow cell division; separating the microalgal cells from culture media, wherein the culture media contains exopolysaccharide molecules produced by the microalgal cells; separating the exopolysaccharide molecules from other molecules present in the culture media; homogenizing the microalgal cells; and adding the separated exopolysaccharide molecules to the cells before, during, or after homogenization. In some embodiments, the microalgal cells are from the genus *Parachlorella*. In other embodiments, the microalgal cells are grown under heterotrophic conditions.

In other embodiments, the invention includes a method of manufacturing a composition comprising particles, the method comprising isolating a polysaccharide from microalgae; drying an aqueous suspension of the polysaccharide to a solid film wherein at least some proportion of the film has been made completely or partially insoluble in water; homogenizing or otherwise milling or disrupting the film into particles; and formulating the particles into a non-aqueous material.

The method may of course be practiced with a variety of microalgal cells capable of producing polysaccharides when cultured under heterotrophic conditions, such as those of the genera *Parachlorella* and *Chlorella*.

As described herein, the resulting composition may be for improving the appearance of skin, such as human skin. In some embodiments, the formulating may be into the oil phase of an oil-in-water emulsion. In other embodiments, the non-aqueous material is an oil suitable for topical administration, with hexadecanoic acid and oil that is contained in an emulsion as non-limiting examples. In further embodiments, the method further comprises formulating the particles into a carrier and/or preservative suitable for topical administration. The resulting composition may also be substantially free of endotoxins and/or protein. In many embodiments, the composition is also made sterile and/or non-pyrogenic. Alternatively, the method further comprises formulating hyaluronic acid into the composition.

In other embodiments, the polysaccharide after the drying step is partially or completely insoluble in water. Optionally, the polysaccharide after the drying step is soluble in water at a percentage selected from the list consisting of less than about 70%, less than about 60%, less than about 50%, less than about 40%, less than about 30%, less than about 20%, less than about 10%, less than about 5%, and less than about 2%.

Embodiments of the drying step include drying performed at between about 40 and about 180° C., such as between about 80° C. and about 170° C., or between about 100° C. and about 160° C., between about 125° C. and about 155° C., between about 135° C. and about 152° C., between about 140° C. and about 150° C., or between about 145° C. and about 148° C. as non-limiting examples. Optionally, the drying is performed in two steps, wherein the first step comprises heating the suspension of the polysaccharide to no more than about 60° C. for a first period of time to produce a solid film followed by heating the solid film for a second period of time to no more than about 160° C. In alternative embodiments, the first and second steps comprise heating to no more than about 80° C. and no more than about 150° C., or to approximately 100° C. and no more than 148° C., respectively. In some embodiments, the suspension of the polysaccharide is heated during the first period of time in the presence of air to produce a solid film and the solid film is heated during the second period of time in at least a partial vacuum or otherwise under reduced pressure.

After the drying step, milling may be by any suitable method. Non-limiting examples include a method selected from the list consisting of jet milling, ball milling, Retsch® milling, and milling in a Quadro® device. The resulting particles of the composition may have an average size between about 400 and about 0.1 microns. In some embodiments, the particles of the composition have an average size between about 100 and about 0.1 microns, between about 50 and about 0.1 microns, between about 10 and about 0.1 microns, between about 10 and about 0.5 microns, or between about 5 and about 0.5 microns.

Examples of carriers suitable for formulating polysaccharide are described above. Ratios of homogenate:carrier are typically in the range of about 0.001:1 to about 1:1 (volume:volume), although the invention comprises ratios outside of this range, such as, but not limited to, about 0.01:1 and about 0.1:1. In some embodiments the ratio of purified polysaccharide:carrier are in the range of about 0.001:1 to about 1:1 (volume:volume), although the invention comprises ratios outside of this range, such as but not limited to, about 0.01:1 and about 0.1:1.

Microalgal cellular extracts can also be formulated for topical administration. It is preferable but not necessary that the cells are physically or chemically disrupted as part of the formulation process. For example, cells can be centrifuged from culture, washed with a buffer such as 1.0 mM phosphate buffered saline, pH 7.4, and sonicated. Preferably the cells are sonicated until the cell walls have been substantially disrupted, as can be determined under a microscope.

Cells can also be dried and ground using means such as mortar and pestle, colloid milling, ball milling, or other physical method of breaking cell walls.

After cell disruption, cell homogenate can be formulated with carrier and fragrance as described above for polysaccharides.

The compositions according to the present invention can also be used as hair treating agents such as hair dressings (e.g., hair creams, hair sprays, hair tonics, hair gels, hair lotions, hair oils, hair essences, hair waters, hair waxes, and hair mousses), shampoos, finishing rinses, hair treatments, hair creams, hair mousses, hair setting lotions, hair colors, hair dyes (e.g., hair colors, one-part hair dyes, and two-part hair dyes), perm solutions (e.g., permanent wave solutions, hair straightening solutions, and permanent wave holding agents), blood flow enhancers, scalp lotions, and anti-hair loss agents. Other applications of the compositions according to the present invention include, for example, skin care cosmetics such as toners, serums, whitening toners, milky lotions, whitening milky lotions, creams, whitening creams, ointments, whitening ointments, lotions, whitening lotions, oils, and facial packs. Furthermore, still other applications of the compositions according to the present invention include, for example, makeup cosmetics such as foundations, liquid foundations, lipsticks, lip glosses, moisturizing lip balms, eye shadows, powders, face powders, blushers, eye shadows, eye liners, mascaras, and eyebrow pencils. Other applications of the compositions according to the present invention include, for example, skin cleaners such as soap, cleansing creams, cleansing lotions, cleansing milks, cleansing pads, cosmetic compositions, facial washes, and body shampoos. Moreover, another application of the compositions according to the present invention is in finishing cosmetics for use in, e.g., manicures. Other applications of the compositions according to the present invention include, for example, cosmetic compositions in the form of bath agents, patches, perfumes, toothpastes, tooth washes, and mouthwashes.

In some embodiments, isolated microalgal polysaccharide can be formulated for human consumption. In some cases, isolated polysaccharide can be formulated in food products as a food ingredient. In such cases, the isolated polysaccharide is grown, isolated and formulated under GMP conditions. In the United States, GMP regulations for manufacturing, packing, or holding human food are codified at 21 C.F.R. 110. These provisions, as well as ancillary provisions referenced therein, are hereby incorporated by reference in their entirety for all purposes. GMP conditions in the Unites States, and equivalent conditions in other jurisdictions, apply in determining whether a food is adulterated (the food has been manufactured under such conditions that it is unfit for food) or has been prepared, packed, or held under unsanitary conditions such that it may have become contaminated or otherwise may have been rendered injurious to health. GMP conditions can include adhering to regulations governing: disease control; cleanliness and training of personnel; maintenance and sanitary operation of buildings and facilities; provision of adequate sanitary facilities and accommodations; design, construction, maintenance, and cleanliness of equipment and utensils; provision of appropriate quality control procedures to ensure all reasonable precautions are taken in receiving, inspecting, transporting, segregating, preparing, manufacturing, packaging, and storing food products according to adequate sanitation principles to prevent contamination from any source; and storage and transportation of finished food under conditions that will protect food against physical, chemical, or undesirable microbial contamination, as well as against deterioration of the food and the container.

In some embodiments, polysaccharide isolated from microalgae of the present invention can be in the form of soluble and insoluble carbohydrates in the form of dietary fiber. In such cases, the polysaccharide can be formulated into a variety of foodstuffs as a food ingredient to add or boost the levels of dietary fiber in the foodstuff. In other embodiments, the polysaccharide can be formulated into foodstuffs as a thickener or as an emulsifier.

Compositions in accordance with the present invention include finished cosmetic products for oral or topical administration. Combinations of various agents suitable or desirable for treatment of skin can be included in such finished cosmetic products. For example, compositions for topical administration can include algal polysaccharides, algal carotenoids, vitamins (e.g., vitamin C, vitamin E, vitamin D, or vitamin D precursors), salicylic acid, amino acids (e.g., tyrosine), amino acid derivatives (e.g., N-acetyl methionine), betaine, perfluoropolyethers, whole cell algae extracts, dihydroxyacetone, *Rhodiola rosea*, menthol, and tissue respiratory factor. Compositions for oral administration can include, for example, fish oils, algal oils, vitamins (e.g., vitamin C, vitamin D, vitamin E), carotenoids, asthaxanthin, zeoxanthin, amino acids (e.g., tyrosine), *Rhodiola rosea*, whole cell algal extracts, and betaine. These components can be combined with suitable carriers, as well as essential oils, fragrance oils, flavor oils, seed oils, botanicals, plant extracts, $CO_2$ extracts, soaps, clays, colorants, titanium dioxide, micas, tinting herbs, glitters, exfoliants, fruit seeds, fibers, grain powders, nut meals, seed meals, oil beads, wax beads, herbs, hydrosols, vitamins, milk powders, preservatives, antioxidants, tocopherols, salts, sugars, vegetable oils, waxes, glycerin, sea vegetables, nutritive oils, moisturizing oils, vegetable butters, propylene glycol, parabens, honey, bees wax, aloe, polysorbate, cornstarch, cocoa powder, coral powder, humectants, gums, emulsifying agents, and/or thickeners.

In some embodiments, compositions in accordance with the present invention include algal polysaccharides in combination with at least one other ingredient selected from the group consisting of beta carotene, lutein, astaxanthin, vitamin C, vitamin E, vitamin A, coenzyme Q10, a peptide, an acylated peptide, oil soluble α-hydroxy acid, an alkyl lactate, and salicylic acid. The polysaccharides and other ingredients can be combined and subjected to processing (e.g., drying, heating, micronization, milling, and the like) to form particles comprising the multiple components for use in cosmetic, skin care, nutraceutical, or other products.

In other embodiments, compositions in accordance with the present invention include algal polysaccharides in combination with at least one other ingredient selected from the group consisting of water, sodium hyaluronate, EDTA, glycerin, shea butter, macadamian oil, isocetyl stearate, olive oil, butylene glycol, amphisol K, PEG 150 disteavate and polyethylene. Optionally, the composition may include a fragrance.

In one aspect, the invention is directed to cosmetic ingredients, including algal polysaccharides encapsulated in microspheres and aqueous solutions of such microencapsulated algal polysaccharides. In some embodiments, the aqueous solutions can include from 0.01% to 10% w/w microencapsulated algal polysaccharides. The microspheres can be formulated to release the algal polysaccharide contents upon topical application to, e.g., human skin, wherein the polysaccharides swell in contact with the skin's moisture to reduce the appearance of wrinkles on the skin. In some embodiments, the when the microalgal polysaccharides have been made partially insoluble and milled into beads with an average diameter of less than 10 microns, the polysaccharide beads can swell to at least 2× volume when in contact with water, as compared to the volume of the dry polysaccharide bead. In other embodiments, the polysaccharide beads swell to at least 5× volume or more when in contact with water.

C. Co-Administered Compositions

Topical compositions can comprise a portion of a complete composition sold as a single unit. Other portions of the complete compositions can comprise an oral supplement intended for administration as part of a regime for altering skin appearance. Because the top layers of the skin contain dead cells, nutrients delivered via capillaries cannot reach the outer layers of cells. The outer layers of cells must be provided with nutrients though topical administration. However, topical administration is not always an effective method of providing nutrients to deep layers of skin that contain living cells. The compositions provided herein comprise both topical compositions that contain algal polysaccharides and/or cellular extracts as well as oral compositions comprising nutraceutical molecules such as purified polysaccharides, whole cell extracts, carotenoids, polyunsaturated fatty acids, and other molecules that are delivered to the skin via capillaries. The combined effect of the topical and oral administration of these molecules and extracts provides a benefit to skin health that is additive or synergistic compared to the use of only a topical or only an orally delivered product.

Examples of the topical components of the composition include exopolysaccharide from *Chlorella* sp., *Parachlorella kessleri*, *Parachlorella beijerinckii*, or other microalgae that are able to produce exopolysaccharides (high molecular weight polysaccahrides that are secreted into the culture medium) when grown under heterotrophic conditions. Other components of the topical composition can include polysaccharides and/or cell extracts from heterotrophically grown microalgae.

Examples of compositions for oral administration include one or more of the following: DHA, EPA, ARA, microalgal oil, lineoileic acid, lutein, lycopene, beta carotene, braunixanthin, zeaxanthin, astaxanthin, linoleic acid, alpha carotene, ascorbic acid (vitamin C), coenzyme Q10, vitamin D, vitamin E, and superoxide dismutase. Compositions for oral administration usually include a carrier such as those described above. Oral compositions can be formulated in tablet or capsule form. Oral compositions can also be formulated in an ingestible form such as a food, tea, liquid, etc. Oral compositions can, for example, comprise at least 50 micrograms, at least 100 micrograms, at least 50 milligrams, at least 100 milligrams, at least 500 milligrams, and at least one gram of a small molecule such as a carotenoids or a polyunsaturated fatty acid.

In another aspect, the invention includes orally administered nutraceutical compositions comprising one or more polysaccharides, or microalgal cell extract or homogenate, of the invention. A nutraceutical composition serves as a nutritional supplement upon consumption. In other embodiments, a nutraceutical may be bioactive and serve to affect, alter, or regulate a bioactivity of an organism.

A nutraceutical may be in the form of a solid or liquid formulation. In some embodiments, a solid formulation includes a capsule or tablet formulation as described above. In other embodiments, a solid nutraceutical may simply be a dried microalgal extract or homogenate, as well as dried polysaccharides per se. In liquid formulations, the invention includes suspensions, as well as aqueous solutions, of polysaccharides, extracts, or homogenates. In some embodiments the nutraceutical is derived from microalgae, while in other embodiments the nutraceutical is derived from other sources such as, for example, plants, plant extracts, and chemically synthesized molecules. In a preferred embodiment a topical composition and an oral composition contain at least one molecule in common.

The methods of the invention include a method of producing a nutraceutical composition. Such a method may comprise drying a microalgal cell homogenate or cell extract. The homogenate may be produced by disruption of microalgae which has been separated from culture media used to propagate (or culture) the microalgae. Thus in one non-limiting example, a method of the invention comprises culturing red microalgae; separating the microalgae from culture media; disrupting the microalgae to produce a homogenate; and drying the homogenate. In similar embodiments, a method of the invention may comprise drying one or more polysaccharides produced by the microalgae.

In some embodiments, a method of the invention comprises drying by tray drying, spin drying, rotary drying, spin flash drying, or lyophilization. In other embodiments, methods of the invention comprise disruption of microalgae by a method selected from pressure disruption, sonication, jet milling and ball milling.

In additional embodiments, a method of the invention further comprises formulation of the homogenate, extract, or polysaccharides with a carrier suitable for human consumption. As described herein, the formulation may be that of tableting or encapsulation of the homogenate or extract.

In further embodiments, the methods comprise the use of microalgal homogenates, extracts, or polysaccharides wherein the cells contain an exogenous nucleic acid sequence, such as in the case of modified cells described herein. The exogenous sequence may encode a gene product capable of being expressed in the cells or be a sequence which increases expression of one or more endogenous microalgal gene product.

In a preferred embodiment, at the topical composition and the oral composition both contain at least one molecule or one type of molecule (such as carotenoids) in common. For example, the topical composition contains homogenate of *Parachlorella* cells that contain zeaxanthin, and the oral composition contains zeaxanthin. In another embodiment, the topical composition contains homogenate of *Parachlorella* cells that contain polysaccharide, and the oral composition contains polysaccharide purified from *Parachlorella* culture media. In another embodiment, the topical composition and the oral composition both contain lutein and/or zeaxanthin. Microalgae can be but need not be the source of either or both lutein and zeaxanthin. In some embodiments, the daily oral composition dosage is about 10 mg lutein and about 0.6 mg zeaxanthin per day, and the daily topical composition dosage is about 100 ppm lutein and about 12 ppm of zeaxanthin in an oil-free liquid. In other embodiments the oral and topical compositions both comprise carotenoids such as at least one of phytoene, phytofluene, beta carotene, lutein, zeaxanthin, and astaxanthin.

In one embodiment, the topical composition, optionally derived or partially derived from microalgae, comprises the carotenoids phytoene and phytofluene, and optionally also contains vitamin C, and vitamin E; the oral composition, optionally derived or partially derived from microalgae, comprises at least two of the following compounds: ascorbic acid, vitamin E succinate, lutein, zeaxanthin, beta carotene, EPA, DHA, and CoQ10. All components of the oral composition do not necessarily need to be formulated into the same tablet or capsule. In some compositions the oral composition comprises at least 3, at least 4, at least 5, at least 6, and at least 7 of the aforementioned compounds. Optionally, daily dosages of the topical composition are about 0.1-7% IBR-CLC® concentrate (phytoene/phytofluene combination; Israeli Biotechnology Research Corp.; U.S. Pat. No. 6,383,474), 1-20% vitamin C, 1-20% vitamin E. Optionally, daily doses for the oral composition are between 20-600 mg ascorbic acid, 20-600 mg vitamin E succinate, 0.1-50 mg lutein, 0.05-30 mg zeaxanthin, 0.1-50 mg beta carotene, 5-400 mg CoQ10, 50-750 mg EPA, and 20-750 mg DHA.

Some of the compositions described herein are packaged for sale as a single unit. For example, a unit for sale comprises a first container holding a composition for topical administration, a second container holding individual doses of a composition for oral administration, and optionally, directions for co-administration of the topical and oral composition. In some embodiments, the composition for topical administration is a cream, lotion, serum, gel, solution, spray or ointment.

Some embodiments of the invention include a combination product comprising 1) a first composition comprising a microalgal extract and a carrier suitable for topical application to skin; and 2) a second composition comprising at least one compound and a carrier suitable for human consumption; wherein the first and second compositions are packaged for sale as a single unit. Thus the invention includes co-packaging of the two compositions, optionally with a instructions and/or a label indicating the identity of the contents and/or their proper use.

Other combination products are including in the invention. In some embodiments, the first composition may be a topical formulation or non-systemic formulation, optionally a cosmeceutical, as described herein. Preferably, the first composition comprises a carrier suitable for topical application to skin, such as human skin. Non-limiting examples of the second composition include a food composition or nutraceutical as described herein. Preferably, the second composition comprises at least one carrier suitable for human consumption, such as that present in a food product or composition. Combination products of the invention may be packaged separately for subsequent use together by a user or packaged together to facilitate purchase and use by a consumer. Packaging of the first and second compositions may be for sale as a single unit.

D. Methods of Cosmetic Enhancement

In a further aspect, the invention includes a method to cosmetically enhance skin or its appearance or texture. In some cases, the enhancement is due to increased or improved skin elasticity. The skin may be that of a human being, such as the skin of the face, hands, feet, or other parts of the human body. In other embodiments, the enhancement may be in the appearance or texture of human lips. The method may comprise administration of a polysaccharide composition suitable for injection into skin or lip tissue to improve the appearance thereof. The composition may be any as described herein suitable for the method of administration or application. In some embodiments, the injection is made to alleviate or eliminate wrinkles. In other embodiments, the treatment reduces the visible signs of aging and/or wrinkles.

As known to the skilled person, human skin, as it ages, gradually loses skin components that keep skin pliant and youthful-looking. The skin components include collagen, elastin, and hyaluronic acid, which have been the subject of interest and use to improve the appearance of aging skin.

The invention includes compositions of microalgal polysaccharides, microalgal cell extracts, and microalgal cell homogenates for use in the same manner as collagen and hyaluronic acid. In some embodiments, the polysaccharides will be those of from a *Parachlorella* species. In some embodiments, the polysaccharides are formulated as a fluid, optionally elastic and/or viscous, suitable for injection. The compositions may be used as injectable dermal fillers as one non-limiting example. The injections may be made into skin to fill-out facial lines and wrinkles. In other embodiments, the injections may be used for lip enhancement. These applications of polysaccharides are non-limiting examples of non-pharmacological therapeutic methods of the invention.

In further embodiments, the microalgal polysaccharides, cell extracts, and cell homogenates of the invention may be co-formulated with collagen and/or hyaluronic acid (such as the Restylane® and Hylaform® products) and injected into facial tissue. Non-limiting examples of such tissue include under the skin in areas of wrinkles and the lips. In a preferred embodiment, the polysaccharide is substantially free of protein. The injections may be repeated as deemed appropriate by the skilled practitioner, such as with a periodicity of about three, about four, about six, about nine, or about twelve months. In another preferred embodiment, a hyaluronic acid material is mixed with a polysaccharide from the genera *Chlorella* or *Parachlorella* prior to co-administration. The invention in this particular embodiment provides longer half-life to the hyaluronic acid due to the potent inhibition of hyaluronidase by polysaccharides isolated from microalgae from the genus *Parachlorella*. This allows for less injections to a patient. Preferably the polysaccharide from the genus *Parachlorella* is at least substantially free of protein. Preferably the mixture of polysaccharide from the genus *Parachlorella* and hyaluronic acid is sterile.

Thus, the invention includes a method of cosmetic enhancement comprising injecting a polysaccharide produced by microalgae into mammalian skin. The injection may be of an effective amount to produce a cosmetic improvement, such as decreased wrinkling or decreased appearance of wrinkles as non-limiting examples. Alternatively, the injection may be of an amount which produces relief in combination with a series of additional injections. In some methods, the polysaccharide is produced by a microalgal species, or two or more species. In one non-limiting example, the microalgal species is of the genus *Parachlorella* and the polysaccharide is substantially free of protein.

The invention includes a method to stimulate elastin synthesis or production in a cell, such as a fibroblast, by contacting the cell with a disclosed polysaccharide. In a related manner, the polysaccharide may also inhibit elastase activity produced by a cell, such as, but not limited to, a fibroblast. In some embodiments, the cell is in the skin of a human subject and the contacting comprises administering the polysaccharide to the subject. The administering may comprise injection of the polysaccharide, or a polysaccharide containing composition of the invention, to the skin or a skin tissue. The amount of polysaccharide administered may be any that is sufficient or effective to stimulate elastin synthesis to a level desired by a skilled person, such as an increase of at least about 50%, 100%, about 200%, or about 300% or higher than that observed in the absence of polysaccharide.

In a related manner, a polysaccharide is used based on its anti-inflammatory in skin or a skin tissue. In some embodiments, the method inhibits polymorphonuclear (PMN) leukocytes in chemotaxis, such as to sites of inflammation in skin. The level of inhibition may be about 10%, about 20%, about 30%, about 40%, or about 50% or more than that seen in the absence of polysaccharide. In other embodiments, the method inhibits the synthesis or release of a pro-inflammatory cytokine, such as interferon-gamma or interleukin-1-alpha. With interferon-gamma as an example, the inhibition may be at least about 10%, about 20%, about 30%, about 40%, about 50%, about 60%, about 70%, about 80%, or about 90% or more than that observed in the absence of polysaccharide. With interleukin-1-alpha as an example, the inhibition may be at least about 10%, about 20%, about 30%, about 40%, about 50%, about 60%, about 70%, or about 80% or more than that observed in the absence of polysaccharide. In further embodiments, the method inhibits proliferation of peripheral blood mononuclear cells, including lymphocytes, monocytes, and macrophages. The level of inhibition may be about 10%, about 20%, about 30%, about 40%, about 50%, about 60%, about 70%, or about 80% or more than that observed in the absence of polysaccharide.

The above described methods may be individually part of a method to reduce the signs of aging or reduce the appearance of aging in human skin as described herein. The methods may also be based upon the insight that the microalgal biomass and polysaccharides of the invention also reduce the effects of UV light or radiation. In some embodiments, the polysaccharide reduces thymidine dimer formation in DNA caused by exposure to UVB irradiation. The reduction may be at least about 10%, about 20%, about 30%, about 40%, about 50%, about 60%, about 70%, or about 80% or more than that observed in the absence of polysaccharide.

In a related manner, the disclosed methods can be used to shield human skin or lip tissue from UV light radiation. The UV radiation may comprise UVA and/or UVB. The method may comprise applying a composition of the disclosed invention to skin or a skin tissue in an effective or sufficient amount to shield, at least in part, the skin from UV radiation. In some embodiments, the amount is that which reduces thymidine dimer formation and/or sunburn. In an alternative embodiment, a composition of the invention may be applied in an effective or sufficient amount, such as that which reduces further UV-mediated damage, to treat skin that has been damaged by UV radiation. An additional non-limiting example is a method of for treating skin to reduce the risk of skin cancer induced by sunlight or UV radiation.

The polysaccharide compositions may be in the form of a sterile and/or non-pyrogenic injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringers solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Hely or a similar alcohol.

Sterile injectable polysaccharide compositions preferably contain less than 1% protein as a function of dry weight of the composition, more preferably less than 0.1% protein, more preferably less than 0.01% protein, less than 0.001% protein, less than 0.0001% protein, more preferably less than 0.00001% protein, more preferably less than 0.000001% protein.

It should be apparent to one skilled in the art that various embodiments and modifications may be made to the invention disclosed in this application without departing from the scope and spirit of the invention. All publications mentioned herein are cited for the purpose of describing and disclosing reagents, methodologies and concepts that may be used in connection with the present invention. Nothing herein is to be construed as an admission that these references are prior art in relation to the inventions described herein.

The following applications are incorporated by reference in their entirety for all purposes: U.S. patent application Ser. No. 11/336,426, filed Jan. 19, 2006, entitled "Polysaccharide Compositions and Methods of Administering, Producing, and Formulating Polysaccharide Compositions"; U.S. patent application Ser. No. 11/337,103, filed Jan. 19, 2006, entitled "Methods and Compositions for Improving the Health and Appearance of Skin"; U.S. patent application Ser. No. 11/336,656, filed Jan. 19, 2006, entitled "Devices and Solutions for Prevention of Sexually Transmitted Diseases"; U.S. patent application Ser. No. 11/336,428, filed Jan. 19, 2006, entitled "Methods and Compositions for Cholesterol Reduction in Mammals"; U.S. patent application Ser. No. 11/337,171, filed Jan. 19, 2006, entitled "Methods and Compositions for Reducing Inflammation and Preventing Oxidative Damage"; U.S. patent application Ser. No. 11/336,431, filed Jan. 19, 2006, entitled "Methods and Compositions for Thickening, Stabilizing and Emulsifying Foods"; U.S. patent application Ser. No. 11/336,430, filed Jan. 19, 2006, entitled "Methods and Compositions for Joint Lubrication"; U.S. Patent Application No. 60/832,091, filed Jul. 20, 2006, entitled "Decolorized Microalgal Compositions for Skin Care Products"; U.S. Patent Application No. 60/838,452, filed Aug. 17, 2006, entitled "Polysaccharide Compositions and Methods of Administering, Producing, and Formulating Polysaccharide Compositions"; U.S. Patent Application No. 60/816,967, filed Jun. 28, 2006, entitled "Zeaxanthin Production Methods and Novel Compositions Containing Zeaxanthin"; U.S. Patent Application No. 60/872,072, filed Nov. 30, 2006, entitled "Polysaccharide Compositions and Methods of Administering, Producing, and Formulating Polysaccharide Compositions"; and PCT Patent Application No: PCT/US2007/001319, filed Jan. 19, 2007, entitled "Nutraceutical Compositions from Microalgae and Related Methods of Production and Administration".

VI. Examples

Example 1

Heterotrophic Growth of Microalgae to Produce Polysaccharides

Chlorella sorokiniana (UTEX 1810), Parachlorella kessleri (strain SAG 27.87) and Parachlorella beijerinckii (strain SAG 2046) were inoculated into autoclaved 1 liter Erlenmeyer flasks containing a nutrient media:

TABLE 1

Nutrient media.

| Component | Final Concentration |
|---|---|
| $NaNO_3$ | 15 mM |
| $CaCl_2 \cdot 2H_2O$ | 0.17 mM |
| $MgSO_4$ | 0.97 mM |
| $K_2HPO_4$ | 0.43 mM |
| $KH_2PO_4$ | 1.28 mM |
| NaCl | 0.43 mM |
| Yeast extract | 4 g/L |
| Glucose | 7% |
| Vitamin Solution | 1x (see below) |
| Trace Minerals | 1x (see below) |

TABLE 2

Nutrient media.

| Vitamin Soln. (1000X) | |
|---|---|
| Tricine | 9 g/L |
| Thiamine HCl | 0.67 g/L |
| Biotin | 0.01 g/L |
| Cyannocobalamin (Vit B 12) | 0.008 g/L |
| Calcium pantothenate | 0.02 g/L |
| p-aminobenzoic acid | 0.04 g/L |
| Trace Mineral 100X | |
| $CuSO4 \cdot 5H2O$ | 0.011 g/L |
| $CoCl2 \cdot 6H2O$ | 0.081 g/L |
| $H3BO3$ | 0.330 g/L |
| $ZnSO4 \cdot 7H2O$ | 1.400 g/L |
| $MnSO4 \cdot H2O$ | 0.810 g/L |
| $Na2MoO4 \cdot 2H2O$ | 0.039 g/L |
| $FeSO4 \cdot 7H2O$ | 0.110 g/L |
| $NiCl2 \cdot 6H2O$ | 0.013 g/L |
| $VOSO4*2H2O$ (Vanadyl (IV)) | 0.039 g/L |
| $Na2O3Se$ (Sodium selinite) | 0.036 g/L |
| Citric Acid Monohydrate | 3.00 g/L |

Media was autoclaved for at least 15 minutes at 121° C.

Parachlorella kessleri and Parachlorella beijerinckii cultures in 1 liter flasks were shielded to prevent exposure to light and were maintained at 28° C. at 200 rpm—1" stroke length for approximately 90-120 hours, until the polysaccharide concentration in the culture media reached between 1-3 g/L. Chlorella sorokiniana culture in 1 liter Fernbach flasks were shielded to prevent exposure to light and were maintained at 28° C. at 200 rpm—1" stroke length for approximately 10 days. The final polysaccharide concentration in the culture media reached between 1-2 g/L. All cultures are fed to maintain a glucose concentration of 1-4%.

Example 2

Isolation and Drying of Polysaccharide

Chlorella sorokiniana, Parachlorella kessleri and Parachlorella beijerinckii cultures were grown as described in Example 1. Dense cultures were centrifuged at 16,000×g at ambient temperature for 30 minutes and the polysaccharides were precipitated from the supernatant with 70% isopropol alcohol (IPA). IPA and the precipitated polysaccharide fibers were poured over a mesh screen. The polysaccharide fibers were collected from the mesh screen and placed in an aluminum weigh boat and subjected to drying in a 60° C. oven for a minimum of two hours. The polysaccharide was sufficiently dried when there was no moisture left in the sample as determined by reaching a constant weight of the sample.

Alternatively, other samples of the same polysaccharide were isolated from the culture medium using tangential flow filtration (TFF). The filters used for the recovery were 0.1 µm PVDF (0.1 m$^2$) (Durapore from Millipore Corp. #P2VVPPC01). Prior to use, the filters were flushed with water (>5 L). Following the filter flush, clarified supernatant was transferred to the recycle tank, and the system configured with both permeate and retentate lines directed back to the TFF tank. The pump speed was set such that the inlet pressure was approximately 7 psig (TMP=3.5 psig), and the permeate monitored at periodic intervals for appearance of full length polysaccharide. This was done by collecting a 10 mL permeate sample and adding 20 mL of IPA, and shaking the solution vigourously. This process was continued (low pressure recycle mode) until the majority of the polysaccharide no longer appeared in the permeate sample (approximately 60-80 minutes). The permeate was then directed to waste and the polysaccharide product was concentrated approximately 50%. After the concentration, the inlet pressure roughly doubled, at which point the diafiltration process was initiated against water. Diafiltration continued for a minimum of 6 times volume exchange, until no significant color was observed in the permeate. Following diafiltration, the material was further concentrated until the inlet pressure reached approximately 25 psig. The material was removed from the system, and the filters were flushed with 100 mL of 37° C. water. Following the flush, the filters were recirculated with 37° C. water for 15 minutes. Both flushes were added to the recovered product. The purified polysaccharide was then transferred to a lyophilizer for drying. The material was flash frozen in the drying tubes (about 500-700 mL per tube) and dried in a lyophilizer for approximately 72 hours. The polysaccharide product was removed, weighed and stored.

Example 3

Monosaccharide Analysis

Purified polysaccharides from *Chlorella sorokiniana*, *Parachlorella kessleri* and *Parachlorella beijerinckii* were subjected to monosaccharide analysis. The cultures were grown as described in Example 1 and the polysaccharide were precipitated from the culture media using isopropanol, collected and dried in 60° C. oven until there was no moisture left.

Monosaccharide analysis was performed by combined gas chromatography/mass spectrometry (GC/MS) of the per-O-trimethylsilyl (TMS) derivatives of the monosaccharide methyl glycosides produced from the sample by acidic methanolysis.

Methyl glycosides prepared from 500 µg of the dry sample was prepared using methanolysis in 1 M HCl in methanol at 80° C. (18-22 hours), followed by re-N-acetylation with pyridine and acetic anhydride in methanol (for detection of amino sugars). The samples were then per-O-trimethylsilylated by treatment with Tri-Sil (Pierce) at 80° C. (30 mins) These procedures were carried out as previously described in Merkle and Poppe (1994) Methods Enzymol. 230: 1-15; York, et al. (1985) Methods Enzymol. 118:3-40. GC/MS analysis of the TMS methyl glycosides was performed on an HP 5890 GC interfaced to a 5970 MSD, using a Supelco DB-1 fused silica capillary column (30 m 0.25 mm ID).

Monosaccharide compositions were determined as follows:

TABLE 3

*Parachlorella kessleri* monosaccharide analysis.

| Glycosyl residue | Mole % |
| --- | --- |
| Arabinose (Ara) | n.d. |
| Rhamnose (Rha) | 33.0 |
| Fucose (Fuc) | n.d. |
| Xylose (Xyl) | 12.9 |
| Glucuronic acid (GlcA) | 3.9 |
| Galacturonic acid (GalA) | n.d. |
| Mannose (Man) | 15.4 |
| Galactose (Gal) | 31.8 |
| Glucose (Glc) | 2.9 |
| N-acetyl galactosamine (GalNAc) | n.d. |
| N-acetyl glucosamine (GlcNAc) | n.d. |

TABLE 4

*Parachlorella beijerinckii* monosaccharide analysis (in Mole %).

| Glycosyl residue | Media 1 | Media 2 |
| --- | --- | --- |
| Arabinose (Ara) | n.d. | n.d. |
| Rhamnose (Rha) | 31.4 | 27.0 |
| Fucose (Fuc) | n.d. | n.d. |
| Xylose (Xyl) | 11.4 | 16.3 |
| Glucuronic Acid (GlcA) | 5.4 | n.d. |
| Mannose (Man) | 18.5 | 18.8 |
| Galactose (Gal) | 30.3 | 35.2 |
| Glucose (Glc) | 2.9 | 2.7 |
| N-acetyl glucosamine (GlcNAc) | n.d | n.d. |
| N-acetyl neuraminic acid (NANA) | n.d. | n.d. |

TABLE 5

*Chlorella sorokiniana* monosaccharide analysis.

| Glycosyl residue | Mole % |
| --- | --- |
| Arabinose (Ara) | 21.6 |
| Rhamnose (Rha) | 17.3 |
| Fucose (Fuc) | n.d. |
| Xylose (Xyl) | 4.0 |
| Glucuronic add (GlcA) | 0.3 |
| Galacturonic acid (GalA) | n.d. |
| Mannose (Man) | 7.1 |
| Galactose (Gal) | 42.0 |
| Glucose (Glc) | 7.8 |
| N-acetyl galactosamine (GalNAc) | n.d. |
| N-acetyl glucosamine (GlcNAc) | n.d. |
| N-acetyl Mannosamine (ManNAc) | n.d. |

Mole % values are expressed as mole percent of total carbohydrate in the sample.
n.d. = none detected.

From the above monosaccharide analysis, the polysaccharides produced from both *Parachlorella* species have a similar monosaccharide profile. It is also possible to alter the monosaccharide profile by growing the microalgae in different nutrient media, in this case, the nitrogen source was altered: NH$_4$ (Media 2) or NO$_3$ (Media 1) was used. As shown above, the same strain of *Parachlorella beijerinckii* grown in two different nutrient media has a different monosaccharide profile. The monosaccharide profile for *Chlorella sorokiniana* contained some differences when compared to the monosaccharide profiles of the two *Parachlorella* strains. The most marked difference was in the mole percentage of Arabinose (at 21.6%, compared to none detected in the two *Parachlorella* strains).

Example 4

Protein Measurement

*Parachlorella kessleri* and *Parachlorella beijerinckii*. were grown as described in Example 1 and polysaccharide from both cultures were purified by IPA precipitation as described in Example 2. The purified polysaccharide from both species of *Parachlorella* was tested for protein content using the Bio Rad Protein Assay, performed according to manufacturer's instructions. Briefly, 10 µl of sample or BSA standard was added with 200 µl of Bio Rad reagent diluted 1:4 in water. Sample was incubated at room temperature for 15 minutes and absorbance at 650 nm was read using a Molecular Devices Spectra Max plate reader. Polysaccahrides from *Parachlorella kessleri* contained 0.64% protein (average of triplicate samples) and polysaccharides from *Parachlorella beijerinckii* contained approximately 1.15% protein (average of triplicate samples).

Example 5

Polysaccharide Bead Production

Purified polysaccharide from *Parachlorella kessleri* and *Parachlorella beijerinckii* were produced from conditions described in Example 1 and purified using either IPA precipitation or the TFF procedures described in Example 2. After the purified polysaccharide was completely dried in a forced air oven at 60° C., an initial grind was performed using a hammer mill. The material was ground to 50-200 µm sized particles (as determined by sifting through a 250 µm mesh screen and microscopic analysis). The polysaccharide powder was then annealed in a forced air oven at 150° C. for 2.5 hours. Following the annealing step, the material described above was ground into paricles or beads of less than 10 µm using an air jet mill. The air jet mill uses compressed high pressure air to grind the dried, purified polysaccharide material.

Example 6

Swelling Properties of Polysaccharide Beads

Purified polysaccharide from *Parachlorella kessleri* and *Parachlorella beijerinckii* were ground and annealed into beads as described in Example 5. To test the swelling properties of the polysaccharide beads, 100 mg of annealed beads was completely dispersed in 10 mL of water in a 15 mL centrifuge tube by vortexing. The samples were then centrifuged for 30 minutes at 20,000×g. Swelling was measured by visual inspection of the polysaccharide gel layer. As shown in FIG. 1, 100 mg of polysaccharide beads produced from purified polysaccharide from *Parachlorella beijerinckii* grown in media containing $NO_3$ (FIG. 1, A) or $NH_4$ (FIG. 1, B) as a nitrogen source, was tested for swelling in 10 mL of water. The polysaccharide in tube A swelled to approximately 2-3× volume as compared to the dry polysaccharide. The polysaccharide in tube B swelled to approximately the 2 mL volume mark in the centrifuge tube. A sample of 100 mg dry polysaccharide beads (*Parachlorella beijerinckii*) is also shown (FIG. 1, C) for comparison. The swelling of the polysaccharide beads upon contact with water is a useful property for topical application to human skin in cosmetic preparations.

Example 7

Viscosity of 1% Solution of Polysaccharide

Viscosity of a 1% solution of purified polysaccharide from *Parachlorella kessleri* and *Parachlorella beijerinckii* was measured. The microalgae were grown under conditions described in Example 1 and the polysaccharides were purified using TFF and lyophilized under conditions described in Example 2. The dried, purified polysaccharides were resuspended in DI $H_2O$ at a 1% w/v concentration. The polysaccharide solution was centrifuged to make sure there were no visible bubbles in the solution. Viscosity was analyzed in a Brookfield Viscometer with an LV3 spindle (#63). The motor was set to 60 rpm and viscosity measurements were taken after 3 minutes. Viscosity measurements for a 1% solution of polysaccharide purified from *Parachlorella kessleri* was 930 cP and from *Parachlorella beijerinckii* was 587 cP.

Example 8

Sulfur Content of Polysaccharide

The sulfur content for purified polysaccharides from *Parachlorella kessleri* and *Parachlorella beijerinckii* was measured. Both microalgae were grown under conditions described in Example 1 and the polysaccharides were purified using TFF and lyophilized under conditions described in Example 2.

Sulfur content was analyzed according to US EPA SW846, Method 6010B, Inductively Coupled Plasma-Atomic Emission Spectrometry. Prior to analysis, the polysaccharide samples were acidified or digested. An appropriate amount of sample was weighed into a microwave vessel to the nearest 0.001 g. The appropriate reagents were then added to the microwave vessel. The vessel was then sealed and placed in the microwave according to the manufactures' directions. The temperature of each vessel reached a minimum of 180±10° C. within 5 minutes and allowed to remain at a minimum of 180±10° C. for 10 minutes. At the end of the microwave program, the vessels were allowed to cool for a minimum of 5 minutes before removal. The vessels were then uncapped and transferred to volumetric flasks for sulfur content analysis. The polysaccharide purified from *Parachlorella kessleri* contained 0.192% sulfur by weight and polysaccharide purified from *Parachlorella beijerinckii* contained 0.68% sulfur by weight.

Example 9

Molecular Weight

Molecular weight of the microalgal polysaccharides were determined using gel permeation chromatography. *Parachlorella kessleri* and *Parachlorella bejerinckii* were grown under conditions described in Example 1. Polysaccharide from both strains were purified using TFF and lyophilized according to conditions described in Example 2. Samples were ground in a mortar and pestle to assure uniformity. Solutions were made at 0.25% (w/v) concentration in the chromatography solvent (0.1N NaCl, 10% acetonitrile). At higher concentrations the samples were too viscous to filter prior to injection. The samples were filtered through 0.45 µm pore size nylon membranes with two Whatman 934-AH spun glass prefilters.

Figure 3A:
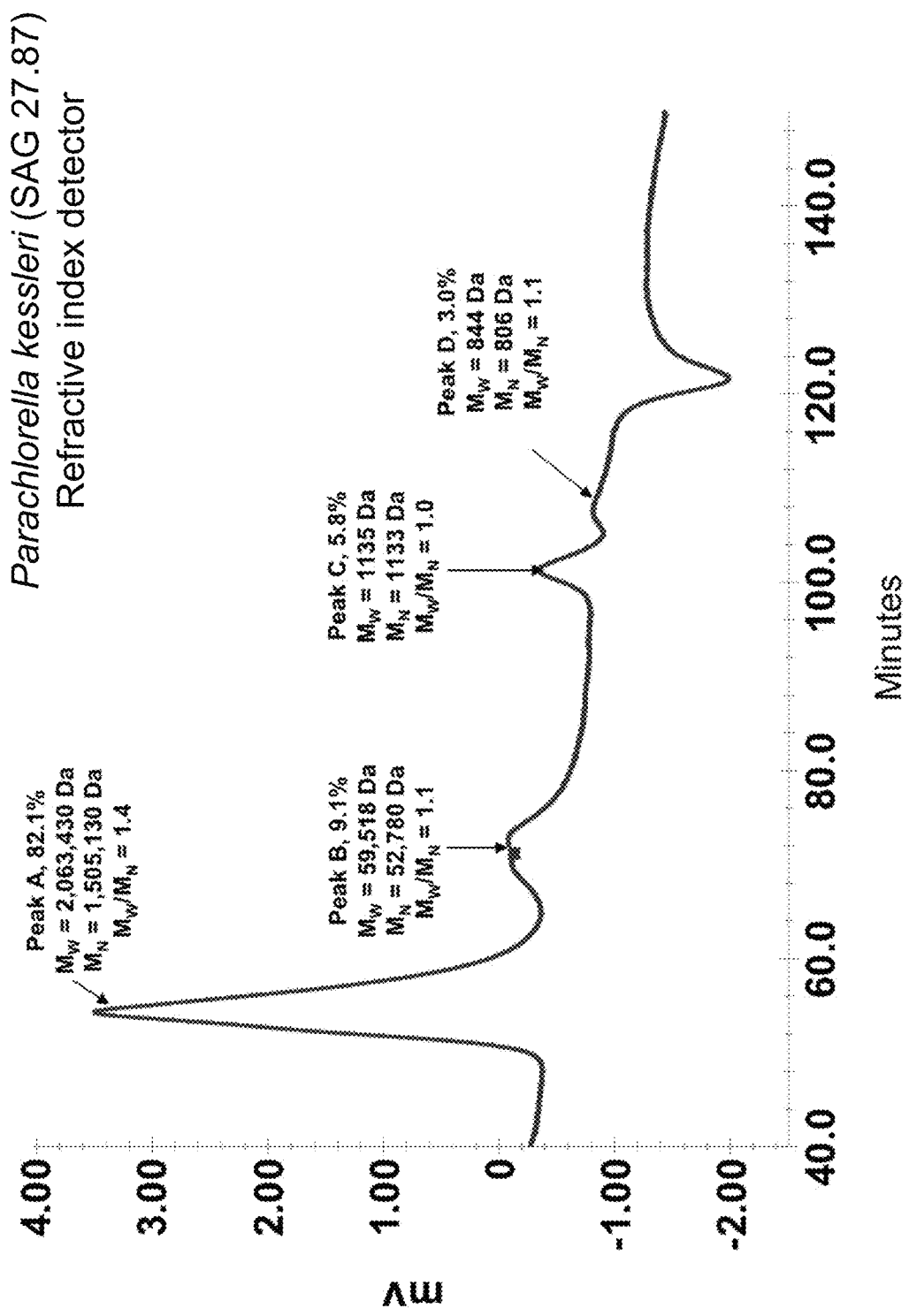
FIGS. 3A and 3B show gel permeation chromatography traces for determining the molecular weights of polysaccharide from *Parachlorella kessleri* and *Parachlorella beijerinckii* using a refractive index detector.
Figure 3B:
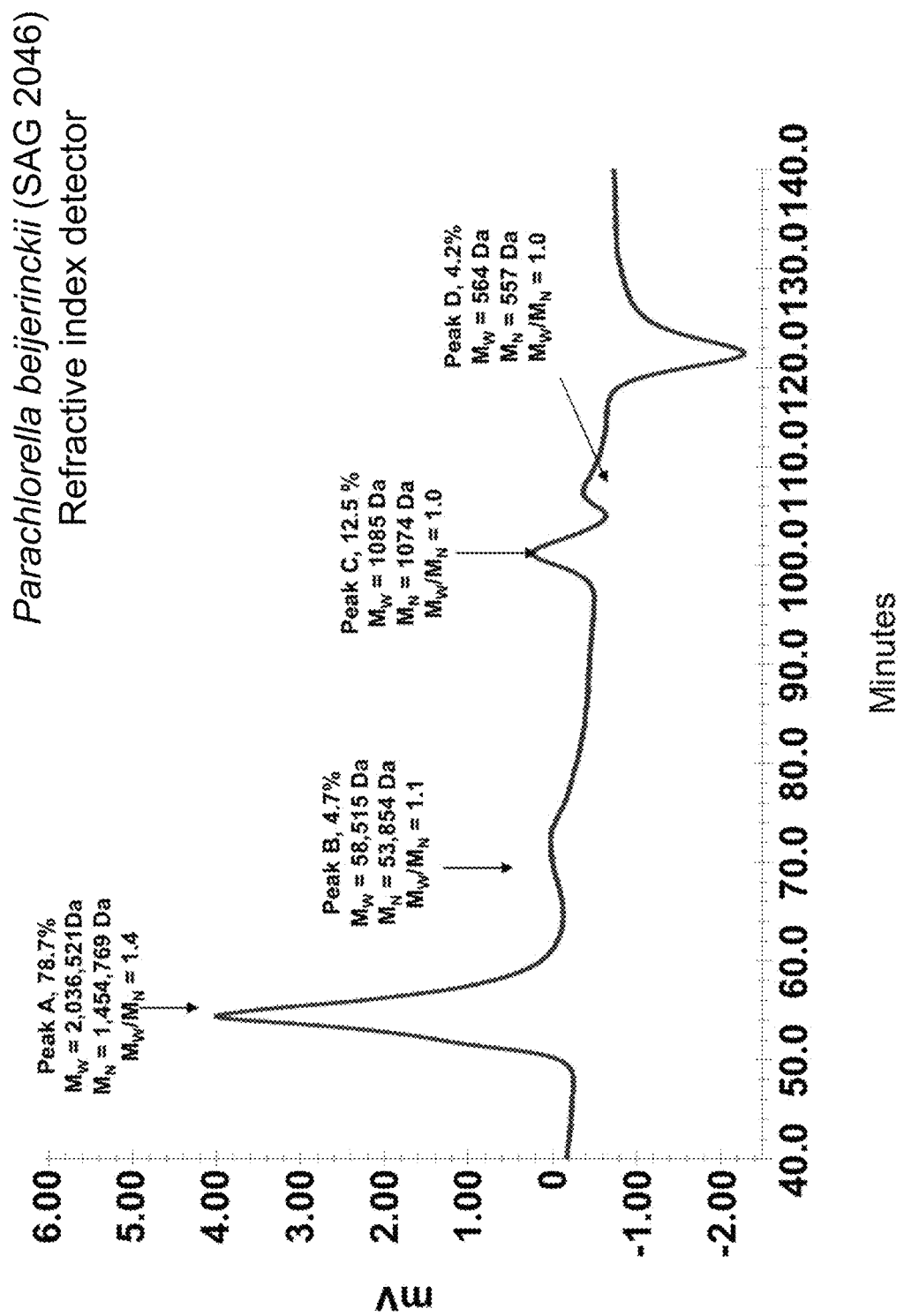

Calibration of the runs against molecular weight standards was performed with narrow molecular weight fractions of dextrans or other water soluble standards such as sodium polystyrene sulfonates. The ratios of peak percentages were determined using the refractive index detector. The ultraviolet detector record absorption from chromophores such as peptides on the polymers and is variable depending on the absorptivity of the groups attached. The columns used for gel permeation chromatography were TSK-gel PWXL in series, G2500, G3000, G4000, G5000, G6000 and shorter precolumn. Results from the refractive index detector are summarized below in Table 6 and the corresponding chromatography traces are shown in FIGS. 3a and 3b. Results from the UV detector were similar and consistent with the refractive index detector results. Both polysaccharide samples eluted off the column as four species of molecules, labeled Peak A, B, C and D. Of the four species, the predominant species (Peak A), making up over 75% of the total sample, had a weight average molecular weight of about 2 million Daltons.

TABLE 6

Molecular weight of purified polysaccharide from *Parachlorella*.

| *Parachlorella kessleri* (SAG 27.87) Refractive Index | | | *Parachlorella beijerinckii* (SAG 2046) Refractive Index | | |
|---|---|---|---|---|---|
| Peak % of total | | Molecular weight, Daltons | Peak % of total | | Molecular weight, Daltons |
| Peak A 82.1% | $M_W =$ $M_N =$ $M_W/M_N =$ | 2,063,430 1,505,130 1.4 | Peak A 78.7% | $M_W =$ $M_N =$ $M_W/M_N =$ | 2,036,521 1,454,769 1.4 |
| Peak B 9.1% | $M_W =$ $M_N =$ $M_W/M_N =$ | 59,518 52,780 1.1 | PeakB 4.7% | $M_W =$ $M_N =$ $M_W/M_N =$ | 58,515 53,854 1.1 |
| Peak C 5.8% | $M_W =$ $M_N =$ $M_W/M_N =$ | 1135 1133 1 | Peak C 12.5% | $M_W =$ $M_N =$ $M_W/M_N =$ | 1085 1074 1.0 |
| Peak D 3.0% | $M_W =$ $M_N =$ $M_W/M_N =$ | 844 806 1.1 | Peak D 4.2% | $M_W =$ $M_N =$ $M_W/M_N =$ | 564 557 1.0 |

$M_W$ = Weight average molecular weight
$M_N$ = Number average molecular weight
$M_W/M_N$ = Polydispersity Example 10

Cosmeceutical Compositions

*Parachlorella kessleri* and *Parachlorella bejerinckii* were grown under conditions described in Example 1. Polysaccharide from both strains were purified using TFF and lyophilized according to conditions described in Example 2. The purified polysaccharide (at 0.1% w/w) was formulated into a night cream with the following ingredients: water, sodium hyaluronate, betaine, trisodium EDTA, glycerin, butylene glycol, amphisol K, shea butter, macadamian oil, isocetyl stearate, olive oil, PEG 150 distearate, grancil VX401, glyceryl monostearate, polyethylene, granpowder USQ, grancil PSQ, diocide and fragrance. The mixture was homogenized to form a composition suitable for topical administration.

Example 11

Skin Irritation/Sensitization Evaluation

Polysaccharide from *Parachlorella beijerinckii* was prepared in a 1% solution for a fifty human subject Repeat Insult Patch Test (RIPT) in order to evaluate if consistent reapplication will cause any irritation/sensitization of human skin. The study was conducted in compliance with CFR Title 21, Part 50 (Informed Consent of Human Subjects). An informed consent was obtained from each volunteer prior to initiating the study, describing reasons for the study, possible adverse effects, associated risks and potential benefits of the treatment and their limits of liability. Fifty subjects (both male and female) ranging from ages 18-66 completed the following study.

Procedure

Subjects were requested to bathe or wash as usual before arrival at the testing facility. 0.2 mL or 0.2 g of the test material was dispensed onto an occlusive, hypoallergenic patch. The patch was applied directly to the skin of the infrascapular regions of the back, to the right or left of the midline and the subject was dismissed with instructions not to wet or expose the test area to direct sunlight. After 24 hours, the patch was removed by the subject at home. This procedure was repeated for a series of nine consecutive 24 hour exposures occurring every Monday, Wednesday and Friday for three consecutive weeks. Subjects were then given a 10-14 day rest period, after which a challenge or retest dose is applied once to a previously unexposed test site. The retest dose was equivalent to any one of the original nine exposures. Reactions were scored 24 and 48 hours after application. Comparison was made between the nine inductive responses and the retest dose. In the event of an adverse reaction, the area of erythema and edema is measured. The edema is estimated by the evaluation of the skin with respect to the contour of the unaffected normal skin. Reactions are scored just before applications two through nine and the next test date following application nine. In most instances, this is approximately 24 hours after patch removal. At the conclusion of the study, the consulting dermatologist reviewed the data and confirmed stated conclusions.

Results

In all 50 subjects, no adverse reactions of any kind were noted during the course of the study. The test material, when tested under occlusion as described above, may be considered a non-primary irritant and non-primary sensitizer to the skin according to *Appraisal of the Safety of Chemicals in Food, Drugs and Cosmetics*, published by The Association of Food and Drug Officials of The United States, 1965 (modified).

Example 12

UV Damage Protection: Prevention of Thymidine Dimer Formation

TFF-purified polysaccharide (see Example 2) from *Parachlorella kessleri* and *Parachlorella beijerinckii* was supplied to the testing site as a 3% stock solution for evaluating changes in tissue DNA thymidine dimer content after exposure to UVB.

The testing system used for this assay was the MatTek EpiDerm®, a skin model that consists of normal human-derived epidermal keratinocytes cultured to form a multi-layered, highly differentiated model of the human epidermis. The tissues were treated topically overnight with either test materials (polysaccharide), 1 mM Trolox (positive control), or left untreated (negative control). On the following day, the tissues were exposed to UVB (300 mJ/cm$^2$). Following the UVB exposures, the DNA was extracted from the EpiDerm tissues using DNEasy Kit (Qiagen) according to manufacturer's instructions. The extracted DNA was quantified via a fluorometric assay. A 10 µl aliquot of the DNA sample was mixed with 1.0 mL TE buffer and 100 µl of this diluted sample was transferred to a well in a 96-well plate. A series of DNA standards (0 to 1000 ng/ml) was also transferred to wells in a 96-well plate in duplicates. Finally, 100 µl of dilute Cyquant Green dye was added to each well and the fluorescence intensity of each well was determined using an excitation wavelength of 480 nm and an emission wavelength of 520 nm.

Aliquots of DNA from the test samples (400 ng in 2×SSC (20× stock SSC: 3M NaCl, 0.3M sodium citrate, pH 7.0)) were loaded onto a membrane via microfiltration blotting. After loading, the membrane was washed once in 2×SSC and then baked for 30 minutes at 80° C. to crosslink the DNA to the membrane. The membrane was then incubated for 1 hour in blocking solution (TBS: 20 mM Tris, pH 7.5, 500 mM NaCl) supplemented with 5% non-fat milk protein, 0.2% polyvinylpyrolidone, and 0.2% ficol), and then briefly washed twice in TBS-T (TBS with 0.1% non-fat milk protein and 0.1% Tween 20). The membrane was then incubated overnight at 4° C. with an antibody that recognizes thymidine dimers diluted in TBS-T. On the following day, the membrane was washed three times with TBS-T (20 minutes per wash) and then incubated with a fluorescently labeled secondary antibody for 1-2 hours at room temperature. After this incubation period the membrane was washed three times with TBS-T (20 minutes per wash). The membrane was placed into a BioRad Molecular Imager FX and scanned using an excitation laser and emission filter combination appropriate for the fluorophore. Images produced by the scanner were then analyzed using ImageJ analysis software. Fluorescence intensity measurements were expressed in Relative Fluorescence Units (RFU). Mean RFU values for each treatment were then calculated and treatments were compared using one way ANOVA.

The results for the thymidine dimer assay are summarized below in Table 7. The values are expressed as RFUs and are presented as mean values±standard deviation. At a 0.03% concentration, both polysaccharide purified from *Parachlorella kessleri* and *Parachlorella beijerinckii* reduced the presence of thymidine dimers in the DNA of the tissues after UVB exposure at a level comparable to that of the positive control (Trolox treated samples). Similar results were seen with polysaccharide purified from *Parachlorella beijerinckii* at a 0.3% concentration (the 0.3% concentration was not performed with polysaccharide from *Parachlorella kessleri*). The results of this study indicate that both of the polysaccharides significantly reduced the amount of thymidine dimer formation.

TABLE 7

| Thymidine dimer assay. | |
|---|---|
| Treatment | RFU |
| Non-UVB exposed | 12 ± 7 |
| Untreated (UVB exposed) | 108 ± 22 |

TABLE 7-continued

| Thymidine dimer assay. | |
|---|---|
| Treatment | RFU |
| Trolox (positive control) | 55 ± 14* |
| 0.03% polysaccharide *P. kessleri* | 59 ± 17* |
| 0.003% polysaccharide *P. kessleri* | 110 ± 31 |
| 0.3% polysaccharide *P. beijerinckii* | 52 ± 11* |
| 0.03% polysaccharide *P. beijerinckii* | 66 ± 18* |
| 0.003% polysaccharide *P. beijerinckii* | 89 ± 9 |

*denotes values that are significantly different from the Untreated group ($p < 0.05$)

Example 13

In Vitro Fibroblast Viability Assay

TFF-purified polysaccharide (see Example 2) from *Parachlorella kessleri* and *Parachlorella beijerinckii* was supplied to the testing site as a 3% stock solution for assessing the viability of fibroblast cells in an in vitro model after exposure to the purified polysaccharides (test materials).

Fibroblasts are cells found in human skin and are the main source of extracellular matrix proteins including the structural proteins, collagen and elastin. A fibroblast cell culture model using a MTT (3-(4,5 Dimethylthiazol-2-yl)-2,5 dipheynyltetrozolium bromide) assay, a colorimetric analysis of the metabolic activity of the cell, can assess the viability of cells (and conversely the toxicity of the test material) after treatment. Reduction of MTT in the mitochondria results in the formation of insoluble purple formazan crystals that are extracted from the cells with isopropanol and quantified spectrophotometrically. The intensity of the purple color is directly proportional to the metabolic activity of the cells and inversely proportional to the toxicity of the test material.

Fibroblasts were seeded into individual wells of a 24-well plate in 0.5 ml of Fibroblast Growth Media (FGM) and incubated overnight at 37° C. and 5% $CO_2$. On the following day the media was removed via aspiration to eliminate any non-adherent cells and replaced with 0.5 ml of fresh FGM. The cells were grown until confluent, with a media change every 48 to 72 hours. Upon reaching confluency, the cells were treated within 24 hours with DMEM supplemented with 1.5% FBS to wash out any effects from the growth factors included in the normal culture media. After this 24-hour wash out period, the cells were treated with purified polysaccharide from *Parachlorella kessleri* and *Parachlorella beijerinckii* at 0.3%, 0.03% and 0.003% concentration. Untreated cells (negative control) just received DMEM with 1.5% FBS. The cells were incubated for 48 hours and at the end of the incubation period, the cell culture medium was removed and the fibroblasts were washed twice with PBS to remove any remaining test material. After the final wash, 500 µl DMEM with 0.5 mg/ml MTT was added to each well and the cells were incubated for 1 hour at 37° C. and 5% $CO_2$. After the incubation, the DMEM/MTT solution was removed and the cells were washed again once with PBS and then 1 ml of isopropyl alcohol was added to the well to extract the purple formazan crystals. 200 µl of isopropanol extracts were transferred to a 96-well plate and the plate was read at 540 nm using isopropyl alcohol as a blank. The mean MTT absorbance value for the negative control cells was calculated and used to represent 100% cell viability. The individual MTT values from the cells undergoing the various treatments were then divided by the mean value for the negative control cells and expressed as a percent to determine the change in cell viability caused by each treatment.

None of the treatment conditions had a significant impact on the viability of the cells and the viability scores for the fibroblasts treated with the test materials were similar to the untreated group. These results are consistent with the conclusion that the test materials were non-toxic to the cells.

Example 14

Elastin Production Assay

Elastin is the main component of a network of elastic fibers that give tissues their ability to recoil after a transient stretch. This protein is released by fibroblasts (soluble elastin) into the extracellular space where it is then cross-linked to other elastin proteins to form an extensive network of fibers and sheets (insoluble elastin). Soluble elastin can be readily measured from cell culture medium via a competitive ELISA-based method.

Fibroblast cells and polysaccharide test materials were prepared as described in Example 13. Untreated cells served as a negative control and cells treated with IGF-1 (100 ng/ml) were used as a positive control. The cells were treated for 48 hours and at the end of the treatment period, cell culture medium from each treatment group was collected and either stored frozen (−75° C.) or assayed immediately. Materials were tested in triplicates.

Soluble alpha-elastin was dissolved in 0.1M sodium carbonate (pH 9.0) at a concentration of 1.25 µg/ml. 150 µl of this solution was then applied to the wells of a 96-well Maxisorp (Nunc) plate and the plate was incubated overnight at 4° C. The wells were then saturated with PBS containing 0.25% BSA (bovine serum albumin) and 0.05% Tween 20. The plate was then incubated with this blocking solution for 1 hour at 37° C. and then washed two times with PBS containing 0.05% Tween 20. A set of alpha-elastin standards was generated ranging from 0 to 100 ng/ml. 180 µl of either standard or test sample (culture medium) was then transferred to a 650 µl microcentrifuge tube. An anti-elastin antibody solution was prepared (the antibody was diluted 1:100 in PBS containing 0.25% BSA and 0.05% Tween 20) and 20 µl of the solution was added to each tube. The tubes were then incubated overnight at 4° C. 150 µl was transferred from each tube to the 96-well elastin ELISA plate, and the plate was incubated for 1 hour at room temperature. The plate was then washed 3 times with PBS containing 0.05% Tween 20. After washing, 200 µl of a solution containing a peroxidase linked secondary antibody diluted in PBS containing 0.25% BSA and 0.05% Tween 20 was added, and the plate was again incubated at room temperature for 1 hour. After washing the plate three times with PBS containing 0.05% Tween 20, 200 µl of a substrate solution was added to the plate and the plate was incubated for 10 to 30 minutes in the dark at room temperature. After this final incubation the plate was read at 460 nm using a plate reader.

To quantify the amount of each substance present, a standard curve was generated using the known concentrations of each substance. A regression analysis was performed to establish the line that best fits these data points. Absorbance values for the test materials and untreated samples were used to estimate the amount of each substance present in each sample. The results are summarized in Table 8 below. The values are presented in mean concentration of elastin±standard deviation of the mean. An increase in elastin production was seen in all treatment conditions with polysaccharide (0.3%, 0.03% and 0.003%). Treatment with the lowest concentration of 0.003% polysaccharide from both *Parachlorella* species produces an increase in elastin production comparable to the positive control (IGF-1).

TABLE 8

Soluble elastin production.

| Treatment | Elastin (ng/ml) |
| --- | --- |
| Untreated (negative control) | 63 ± 20 |
| IGF-1 (100 ng/ml) | 108 ± 15* |
| 0.3% polysaccharide *P. kessleri* | 86 ± 7 |
| 0.03% polysaccharide *P. kessleri* | 97 ± 18 |
| 0.003% polysaccharide *P. kessleri* | 120 ± 15* |
| 0.3% polysaccharide *P. beijerinckii* | 97 ± 23 |
| 0.03% polysaccharide *P. beijerinckii* | 99 ± 9 |
| 0.003% polysaccharide *P. beijerinckii* | 107 ± 12* |

*denotes values that are significantly different from Untreated group ($p < 0.05$).

Example 15

Peripheral Blood Mononuclear Cell (PBMC) Proliferation Assay and Cytokine Analysis When presented with certain antigens, lymphocytes, which are the main cell type in PBMCs, respond by proliferating. This proliferation happens in an inflammatory response and the lymphocytes also secrete factors, termed cytokines, that recruit other immune cells and/or sustains the proliferation of lymphocytes. In vitro methods recreate this initial proliferation event by using PBMCs and antigens, such as phytohemagglutinin (PHA) to stimulate a proliferation response. A vital dye, such as 3-(4,5-dimethylthiazol-2-yl)-5-(3-carboxymethoxyphenyl)-2-(4-sulfophenyl)-2H-tetrazolium (MTS) can be used to quantify the extent of proliferation. MTS can be taken up by cells and active dehydrogenase enzymes within the viable cells convert the MTS to a water soluble formazan product. This formazan product accumulates in the cell culture media in proportion to the number of viable cells and can be measured spectrophotometrically. Agents can then be screened in this assay to assess their ability to modulate this inflammatory response. If there is a decrease in proliferation upon treatment with an agent, then this is correlative to an anti-inflammatory effect. Alternatively, if there is an increase in proliferation upon treatment with an agent, then this is correlative to a pro-inflammatory effect. Additionally, the cell culture media can be collected and assayed for secreted cytokines such as IL-1 and gamma interferon. These cytokines are known to be upregulated during inflammation.

Polysaccharide test materials, prepared as described in Example 13, were tested for anti-inflammatory properties using the above described PBMC in vitro assay. 100 µl of PBMCs (thawed from cryopreserved vials at a concentration of 1× 106 cells/ml) were added to wells in a 96 well place (each treatment was tested in triplicate). 100 µl of media supplemented with 2.5 µg/ml PHA and the polysaccharides (at 0.003, 0.03 and 0.3% final concentration) were added to the wells. Cyclosporin A (2.5 µg/ml), a known anti-inflammatory compound, was used as a positive control, while cells that received no test agent (PHA only, untreated cells) were used as a negative control. One set of cells that was not treated with PHA served as a baseline reference for all of the measurements (non-stimulated). After the cells had been prepared, the plates were incubated for approximately 68 hours at 37° C. and 5% CO2. After the incubation, 30 µl of MTS solution was added to each well and the 96-well plate was returned to the incubator for an additional 4 hours. The plate was then read at 490 nm using a plate reader. A second set of plates was also prepared and treated as described above. At the end of the incubation period, the cell culture supernatant was assayed for IL-1alpha and gamma interferon secretion.

IL-1alpha secretion was measured using an ELISA. The ELISA plates were prepared by diluting IL-1alpha capture antibodies in PBS. Next 100 µl of the diluted capture antibody was added to the wells of a 96-well ELISA plate and was incubated overnight at room temperature. On the following day, the plate was washed three times with 300 µl wash buffer (0.05% Tween 20 in PBS) and then blocked by adding 300 µl of blocking buffer (1% BSA in PBS) to each well. The plate was incubated with the blocking buffer for at least one hour at room temperature. After the incubation, the plate was washed three times with wash buffer. A series of standards was prepared (0 to 500 pg/ml of recombinant IL-1alpha) and 100 µl of each of these standards was dispensed into two wells as duplicates in the appropriate 96 well plate. 100 µl of media from each test condition (in triplicates) was also added to the 96 well plate and incubated at room temperature for 2 hours. After incubation, the plate was washed three times with wash buffer. 100 µl of biotin conjugated detection antibody was added and the plate was incubated at room temperature for 2 hours. The plate was washed again for three times and 100 µl of HRP-streptavidin was then added to each well and the plate was incubated at room temperature for 20 minutes. The plate was washed three times with wash buffer and the 100 µl of substrate solution (hydrogen peroxide+tetramethylbenzidine) was added to each well. Once a sufficient level of color development had occurred, 50 µl of stop solution (2N sulfuric acid) was added to each well and the plate was read at 460 nm. Gamma interferon secretion was also assayed using an ELISA using the same methods as the IL-1alpha ELISA, but with a gamma interferon capture antibody.

Treatment with 0.3% final concentration of both polysaccharides (from *Parachlorella kessleri* and *Parachlorella beijerinckii*) was observed to significantly reduce the amount of PHA-stimulated proliferation of PBMCs. With respect to cytokine release (IL-1alpha and gamma interferon), both polysaccharides were observed to significantly reduce the amount of PHA-stimulated IL-1alpha and gamma interferon secretion in a dose dependent manner. These results indicate that both polysaccharides were able to produce an anti-inflammatory effect on PBMCs in vitro and may be able to reduce inflammation in vivo. The results of this study are summarized in Table 9 below. The results for the PBMC proliferation assay ware expressed as a stimulation index, using the untreated PBMC not exposed to PHA (non-stimulated) to represent 100%. All values for these assays are expressed as means±standard deviation.

TABLE 9

PBMN activation assay results.

| Treatment | Proliferation Assay (stimulation index) | IL-1 alpha ELISA (pg/ml) | Gamma interferon ELISA (pg/ml) |
|---|---|---|---|
| Non-stimulated | 100 ± 4 | 257 ± 385 | 5 ± 4 |
| Untreated (negative control) | 254 ± 17 | 14203 ± 519 | 201 ± 3 |
| 2.5 µg/ml cyclosporin A (positive control) | 98 ± 7* | 1586 ± 649* | 77 ± 11* |
| Polysaccharide (*P. kessleri*) 0.3% | 170 ± 16* | 2167 ± 877* | 116 ± 3* |
| Polysaccharide (*P. kessleri*) 0.03% | NS | 8613 ± 2685* | 144 ± 22* |
| Polysaccharide (*P. kessleri*) 0.003% | NS | 18027 ± 2045 | 114 ± 7* |
| Polysaccharide (*P. beijerinckii*) 0.3% | 207 ± 25* | 570 ± 519* | 107 ± 3* |
| Polysaccharide (*P. beijerinckii*) 0.03% | NS | 4788 ± 679* | 130 ± 13* |
| Polysaccharide (*P. beijerinckii*) 0.003% | NS | 9365 ± 2203* | 117 ± 11* |

*denotes values that are significantly different from the Untreated group ($p < 0.05$)
NS denotes non-significant value Example 16

Genotyping of Polysaccharide Producing Microalgae Strains

Several strains of microalgae from the genus *Chlorella* and *Parachlorella* were grown heterotrophically grown under conditions described in Example 1 and genotyped according to 23S rRNA genomic sequence. The strains were: *Chlorella sorokiniana* UTEX 1810, *Parachlorella kessleri* SAG 27.87, and *Parachlorella beijerinckii* SAG 2046. Genomic DNA was isolated from algal biomass as follows: Cells (approximately 200 mg) were centifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and the tubes containing the biomass and bead were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes.

The resulting pellet was then washed twice with 70% ethanol, followed by a final wash with 100% ethanol. Pellets were air dried for 20-30 minutes at room temperature followed by resuspension in 50 μl of 10 mM TrisCl, 1 mM EDTA (pH 8.0).

Figure 2:
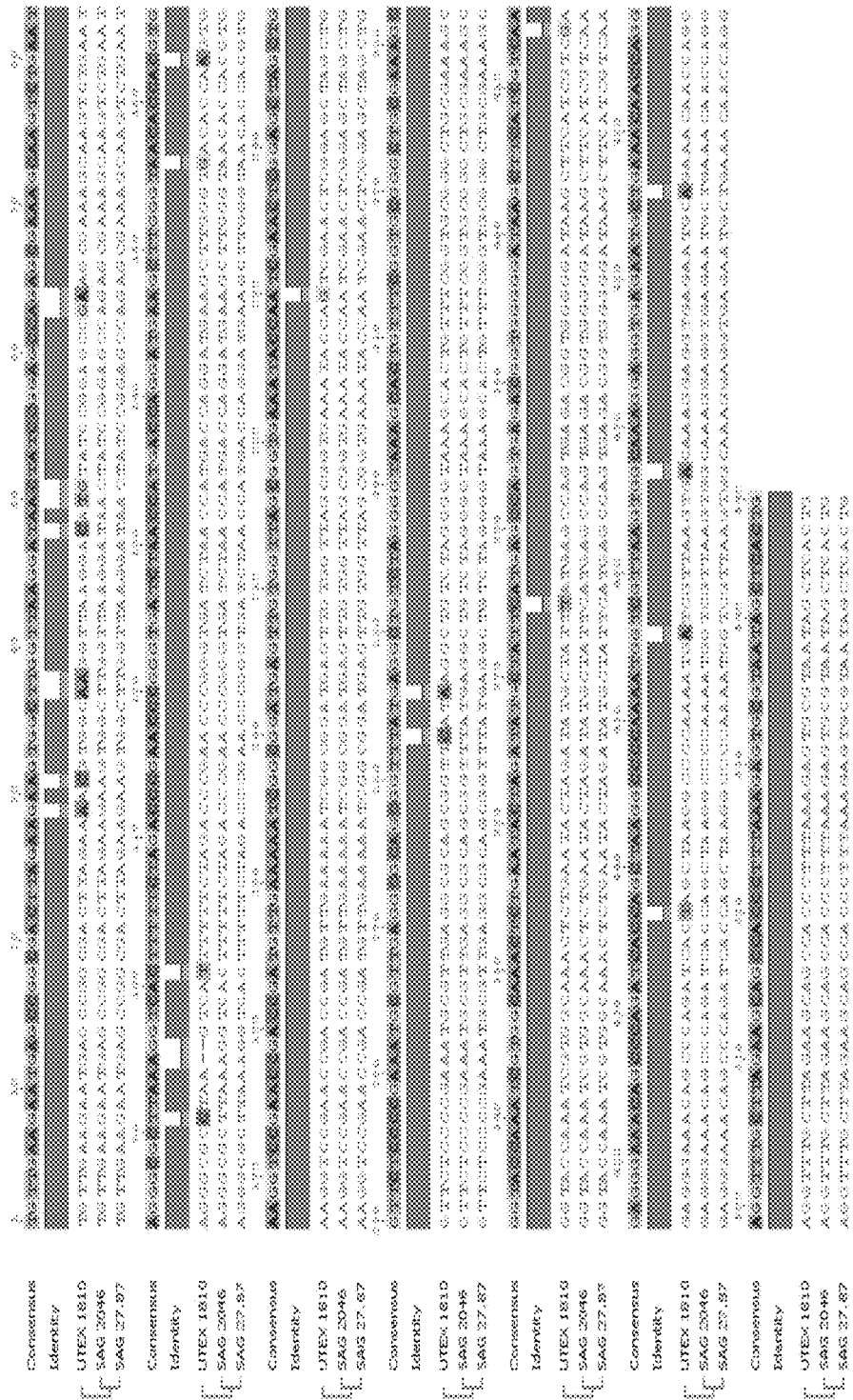
FIG. 2 shows a Cladogram comparison of 23S rRNA genomic sequences from *Parachlorella kessleri* (SAG 27.87), *Parachlorella beijerinckii* (SAG 2046) and *Chlorella sorokiniana* (UTEX 1810).

Five μl of total algal DNA, prepared as described above, was diluted 1:50 in 10 mM Tris, pH 8.0. PCR reactions, final volume 20 μl, were set up as follows. Ten μl of 2×iProof HF master mix (BIO-RAD) was added to 0.4 μl primer SZ02613 (5'-TGTTGAAGAATGAGCCGGCGAC-3' (SEQ ID NO:1) at 10 mM stock concentration). This primer sequence runs from position 567-588 in Gen Bank accession no. L43357 and is highly conserved in higher plants and algal plastid genomes. This was followed by the addition of 0.4 μl primer SZ02615 (5'-CAGTGAGCTATTACGCACTC-3' (SEQ ID NO:2) at 10 mM stock concentration). This primer sequence is complementary to position 1112-1093 in Gen Bank accession no. L43357 and is highly conserved in higher plants and algal plastid genomes. Next, 5 μl of diluted total DNA and 3.2 μl dH$_2$O were added. PCR reactions were run as follows: 98° C., 45 seconds; 98° C., 8 seconds; 53° C., 12 seconds; 72° C., 20 seconds for 35 cycles followed by 72° C. for 1 mM and holding at 25° C. For purification of PCR products, 20 μl of 10 mM Tris, pH 8.0, was added to each reaction, followed by extraction with 40 μl of Phenol:Chloroform: isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. Sequences from the above strains are listed as SEQ ID NOs: 3-4 in the attached Sequence Listing. Strains SAG 27.87 and SAG 2046 had identical 23S rRNA genomic sequences and the 23S rRNA genomic sequence of UTEX 1810 was approximately 96% identical to that of the other strains tested. A Cladogram comparing the sequence results from all three microalgal strains is shown in FIG. 2.

Example 17

Fed Batch Production of Polysaccharides

*Parachlorella kessleri* (SAG 27.87) and *Parachlorella beijerinckii* (SAG 2046) were grown in fed-batch cultures in 7 L fermentors to produce soluble exopolysaccharides. The media formulation was: K2HPO4 (0.14 g/L); NaH2PO4 (0.11 g/L); MgSO4.7H2O (0.37 g/L); (NH4)2SO4 (1.00 g/L); CaCl2.2H2O (0.03 g/L); yeast extract (Amberex) (4.00 g/L); citric acid (0.25 g/L); 100× C-trace elements (10 mL/L); Antifoam 204 (Sigma) (0.225 mL/L); and 1000× DAS vitamins (1 mL/L). Cultures were inoculated at 7% v/v and the temperature was kept at 28° C. and a pH of 6.8. 10% KOH and 10% HCl were added in order to keep the pH level at 5.0 through out the fermentor run. Cultures were agitated at 200 rpm for the first 52 hours and then increased to 350 rpm for the rest of the culture time. Glucose levels were adjusted so that it was maintained at between 5-30 grams/liter throughout the run. The fermentation run for *Parachlorella kessleri* lasted for 190 hours (approx. 8 days) and achieved a polysaccharide titer of 1.35 grams/liter. The fermentation run for *Parachlorella beijerinckii* lasted for 333 hours (approx. 14 days) and achieved a polysaccharide titer of 2.6 grams/liter. The resulting polysaccharides were purified using TFF methods described in Example 2 and dried and weighed.

Example 18

Monosaccharide Analysis

Purified polysaccharide from *Parachlorella kessleri* and *Parachlorella beijerinckii* from fed batch cultures (purified by TFF under conditions described in Example 2) were subjected to monosaccharide analysis.

Monosaccharide analysis was performed by combined gas chromatography/mass spectrometry (GC/MS) of the per-O-trimethylsilyl (TMS) derivatives of the monosaccharide methyl glycosides produced from the sample by acidic methanolysis.

Methyl glycosides prepared from 500 μg of the dry sample was prepared using methanolysis in 1 M HCl in methanol at 80° C. (18-22 hours), followed by re-N-acetylation with pyridine and acetic anhydride in methanol (for detection of amino sugars). The samples were then per-O-trimethylsilylated by treatment with Tri-Sil (Pierce) at 80° C. (30 mins) These procedures were carried out as previously described in Merkle and Poppe (1994) Methods Enzymol. 230: 1-15; York, et al. (1985) Methods Enzymol. 118:3-40. GC/MS analysis of the TMS methyl glycosides was performed on an HP 5890 GC interfaced to a 5970 MSD, using a Supelco DB-1 fused silica capillary column (30 m 0.25 mm ID).

Monosaccharide compositions were determined as follows:

TABLE 10

*Parachlorella kessleri* monosaccharide analysis.

| Glycosyl residue | Mole % |
|---|---|
| Ribose (Rib) | n.d. |
| Rhamnose (Rha) | 52.8 |
| Fucose (Fuc) | n.d. |
| Xylose (Xyl) | 26.6 |
| Glucuronic acid (GlcA) | 9.8 |
| Galacturonic acid (GalA) | n.d. |
| Mannose (Man) | 2.2 |
| Galactose (Gal) | 7.5 |
| Glucose (Glc) | 1.0 |
| A-acetyl galactosamine (GalNAc) | n.d. |
| Methyldeoxyhexose | + |
| Hexadecanoic Acid* | + |
| Octadecadienoic Acid* | + |

TABLE 11

*Parachlorella beijerinckii* monosaccharide analysis.

| Glycosyl residue | Mole % |
|---|---|
| Rhamnose (Rha) | 50.1 |
| Xylose (Xyl) | 31.2 |
| Glucuronic Acid (GlcA) | 11.5 |
| Mannose (Man) | 1.4 |
| Galactose (Gal) | 4.3 |
| Glucose (Glc) | 1.4 |
| N-acetyl galactosamine (GalNAc) | n.d |
| N-acetyl glucosamine (GlcNAc) | n.d. |
| 3 Deoxy-2-manno-2 Octuslsonic acid (KDO) | n.d |
| Methyldeoxyhexose | + |
| Hexadecanoic Acid* | + |
| Octadecadienoic Acid* | + |
| Octadecenoic Acid* | + |

Mole % values are expressed as mole percent of total carbohydrate in the sample.
n.d. = none detected.
+ = detected at below quantitative levels (below about 1-3%)
*Fatty acids were detected but were not quantitated because conditions were setup for monosaccharide quantitation.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A product suitable for topical administration, comprising:
   isolated exopolysaccharide from microalgae of the species *Parachlorella kessleri* or *Parachlorella beijerincki*, wherein the monosaccharide content of the exopolysaccharide comprises 15-55 mole percent rhamnose, 3-30 mole percent xylose, 1-25 mole percent mannose, 1-45 mole percent galactose, 0.5-10 mole percent glucose, and 0.1-15 mole percent glucuronic acid, and wherein the exopolysaccharide is prepared by drying and annealing at a temperature of between about 125° C. and about 155° C. so as to form particles that are partially soluble in water and increase in volume at least two-fold upon contact with water compared to the anhydrous volume of the exopolysaccharide particles; and
   at least one other cosmetic ingredient.

2. The product of claim 1, wherein the exopolysaccharide has been milled to provide exopolysaccharide particles having an average particle size of between about 400 microns and about 0.1 microns.

3. The product of claim 1, wherein the average particle size of the exopolysaccharide particles is between about 50 microns and about 200 microns.

4. The product of claim 2, wherein the exopolysaccharide particles resuspended in water have a viscosity of between about 500 cP and about 1000 cP.

5. The product of claim 1, wherein the at least one other cosmetic ingredient is selected from the group consisting of beta carotene, lutein, astaxanthin, vitamin C, vitamin E, vitamin A, coenzyme Q10, a peptide, an acylated peptide, oil soluble a-hydroxy acid, an alkyl lactate, and salicylic acid.

6. The product of claim 1, wherein the at least one other cosmetic ingredient is selected from the group consisting of water, sodium hyaluronate, betaine, trisodium EDTA, glycerin, blutylene glycol, amphisol K, shea butter, macadamian oil, isocetyl stearate, olive oil, PEG 150 distearate, grancil VX401, glyceryl monostearate, polyethylene, granpowder USQ, grancil PSQ, diocide and fragrance.

7. The product of claim 1 that is a cream, lotion, serum, gel, solution, spray or ointment.

8. The product of claim 1, wherein the exopolysaccharide particles are from *Parachlorella kessleri*.

9. A product suitable for topical administration, comprising:
   isolated exopolysaccharide from microalgae of the species *Chorella sorokiniana*, wherein the monosaccharide content of the exopolysaccharide comprises 15-55 mole percent rhamnose, 3-30 mole percent xylose, 1-25 mole percent mannose, 1-45 mole percent galactose, 0.5-10 mole percent glucose, and 0.1-15 mole percent glucuronic acid, and wherein the exopolysaccharide is prepared by drying and annealing at a temperature of between about 125° C. and about 155° C. so as to form particles that are partially soluble in water and increase in volume at least two-fold upon contact with water compared to the anhydrous volume of the exopolysaccharide particles; and
   at least one other cosmetic ingredient.

10. The product of claim 9, wherein the exopolysaccharide has been milled to provide exopolysaccharide particles having an average particle size of between about 400 microns and about 0.1 microns.

11. The product of claim 9, wherein the average particle size of the exopolysaccharide particles is between about 50 microns and about 200 microns.

12. The product of claim 10, wherein the exopolysaccharide particles resuspended in water have a viscosity of between about 500 cP and about 1000 cP.

13. The product of claim 9, wherein the at least one other cosmetic ingredient is selected from the group consisting of beta carotene, lutein, astaxanthin, vitamin C, vitamin E, vitamin A, coenzyme Q10, a peptide, an acylated peptide, oil soluble a-hydroxy acid, an alkyl lactate, and salicylic acid.

14. The product of claim 9, wherein the at least one other cosmetic ingredient is selected from the group consisting of water, sodium hyaluronate, betaine, trisodium EDTA, glycerin, blutylene glycol, amphisol K, shea butter, macadamian oil, isocetyl stearate, olive oil, PEG 150 distearate, grancil VX401, glyceryl monostearate, polyethylene, granpowder USQ, gransil PSQ, diocide and fragrance.

15. The product of claim 9 that is a cream, lotion, serum, gel, solution, spray or ointment.

16. The product of claim 1, wherein the exopolysaccharide particles are from *Parachlorella beijerinckii*.

17. The product suitable for topical administration of claim 1, wherein the microalgae species have at least 95% 23 S rRNA genomic sequence identity to SEQ ID NO:3.

18. The product suitable for topical administration of claim 9, wherein the microalgae species have at least 95% 23 S rRNA genomic sequence identity to SEQ ID NO: 4.

* * * * *